(12) United States Patent  
Sakai

(10) Patent No.: US 12,187,023 B2  
(45) Date of Patent: Jan. 7, 2025

(54) STRETCHABLE MEMBER AND DISPOSABLE WEAR ARTICLE USING STRETCHABLE MEMBER

(71) Applicant: Daio Paper Corporation, Ehime (JP)

(72) Inventor: Syunsuke Sakai, Tochigi (JP)

(73) Assignee: Daio Paper Corporation, Ehime (JP)

( * ) Notice: Subject to any disclaimer, the term of this patent is extended or adjusted under 35 U.S.C. 154(b) by 1040 days.

(21) Appl. No.: 16/961,812

(22) PCT Filed: Mar. 11, 2019

(86) PCT No.: PCT/JP2019/009572  
§ 371 (c)(1),  
(2) Date: Jul. 13, 2020

(87) PCT Pub. No.: WO2019/181588  
PCT Pub. Date: Sep. 26, 2019

(65) Prior Publication Data  
US 2021/0069029 A1 Mar. 11, 2021

(30) Foreign Application Priority Data  
Mar. 19, 2018 (JP) .................................. 2018-051154

(51) Int. Cl.  
*B32B 7/14* (2006.01)  
*A61F 13/15* (2006.01)  
(Continued)

(52) U.S. Cl.  
CPC ............... *B32B 7/14* (2013.01); *B32B 5/022* (2013.01); *B32B 5/26* (2013.01);  
(Continued)

(58) Field of Classification Search  
CPC .... A61F 13/49; A61F 13/4906; A61F 13/496; A61F 13/5655; A61F 2013/15552;  
(Continued)

(56) References Cited

U.S. PATENT DOCUMENTS 5,576,090 A * 11/1996 Suzuki .............. A61F 13/15593  
428/152  
8,197,458 B2 * 6/2012 Back ..................... B29C 65/02  
604/396  
(Continued)

FOREIGN PATENT DOCUMENTS

EP 3251644 A1 12/2017  
EP 3251642 B1 8/2020  
(Continued)

OTHER PUBLICATIONS

International Search Report for PCT/JP2019/009572, mailed Jun. 4, 2019.

*Primary Examiner* — Philip R Wiest  
*Assistant Examiner* — Linnae E. Raymond  
(74) *Attorney, Agent, or Firm* — Andrus Intellectual Property Law, LLP

(57) ABSTRACT

To prevent or suppress the occurrence of tearing of an elastic film between stretchable regions in an elastic sheet stretchable structure. An elastic sheet stretchable structure is provided, in which an elastic film is laminated between a first sheet layer having air permeability and a second sheet layer having air permeability, and the first sheet layer and the second sheet layer are bonded at a large number of sheet bonded portions arranged at intervals. At the boundary between a first stretchable region and a second stretchable region, a separation distance Px in an elastic limit elongation state between a bonded portion located on a side of the boundary of the first stretchable region in a stretchable direction and a bonded portion located on a side of the boundary of the second stretchable region in a stretchable direction is 10 mm or less.

8 Claims, 33 Drawing Sheets

(51) Int. Cl.
*A61F 13/49* (2006.01)
*B29C 65/00* (2006.01)
*B29C 65/08* (2006.01)
*B29L 31/48* (2006.01)
*B32B 5/02* (2006.01)
*B32B 5/26* (2006.01)

(52) U.S. Cl.
CPC ............... *A61F 2013/15552* (2013.01); *A61F 2013/49023* (2013.01); *A61F 2013/49033* (2013.01); *A61F 13/4906* (2013.01); *B29C 65/08* (2013.01); *B29C 66/21* (2013.01); *B29L 2031/4878* (2013.01)

(58) Field of Classification Search
CPC .. A61F 2013/49023; A61F 2013/49033; A61F 13/514; A61F 13/49009–4902; A61F 2013/49022–49057; B29C 66/01–496; B32B 7/04–14
See application file for complete search history.

(56) References Cited

U.S. PATENT DOCUMENTS

| | | | | |
|---|---|---|---|---|
| 8,449,519 B2* | 5/2013 | Een | ..................... | B29C 66/1122 604/392 |
| 2006/0149209 A1* | 7/2006 | Malchow | ........... | A61F 13/5655 604/389 |
| 2019/0133846 A1* | 5/2019 | Shirai | ............... | A61F 13/51478 |
| 2019/0374398 A1* | 12/2019 | Coenen | ............ | A61F 13/15593 |

FOREIGN PATENT DOCUMENTS

| | | | | |
|---|---|---|---|---|
| JP | 2009148447 A | 7/2009 | | |
| JP | 2015-204982 | 11/2015 | | |
| JP | 2016-140477 | 8/2016 | | |
| JP | 5967736 | 8/2016 | | |
| JP | 2018-110635 | 7/2018 | | |
| WO | WO-2012036600 A1 * | 3/2012 | ......... | A61F 13/4902 |
| WO | 2016121975 A1 | 8/2016 | | |
| WO | 2016121980 A1 | 8/2016 | | |

\* cited by examiner

[FIG.10]
(a)
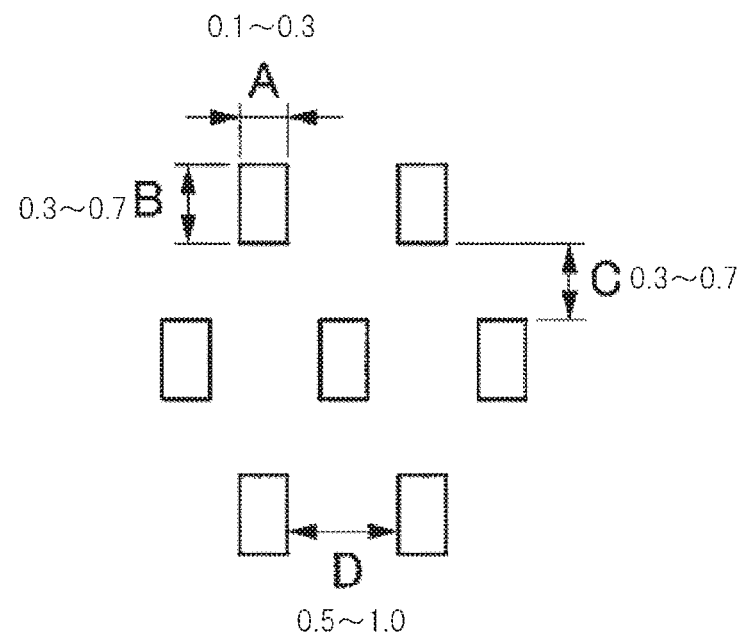
(b)
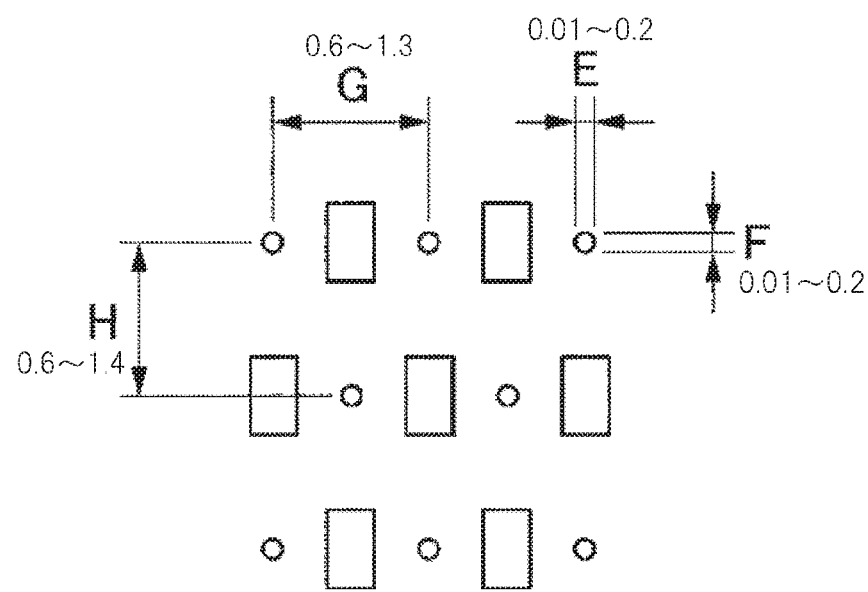

[FIG.11]
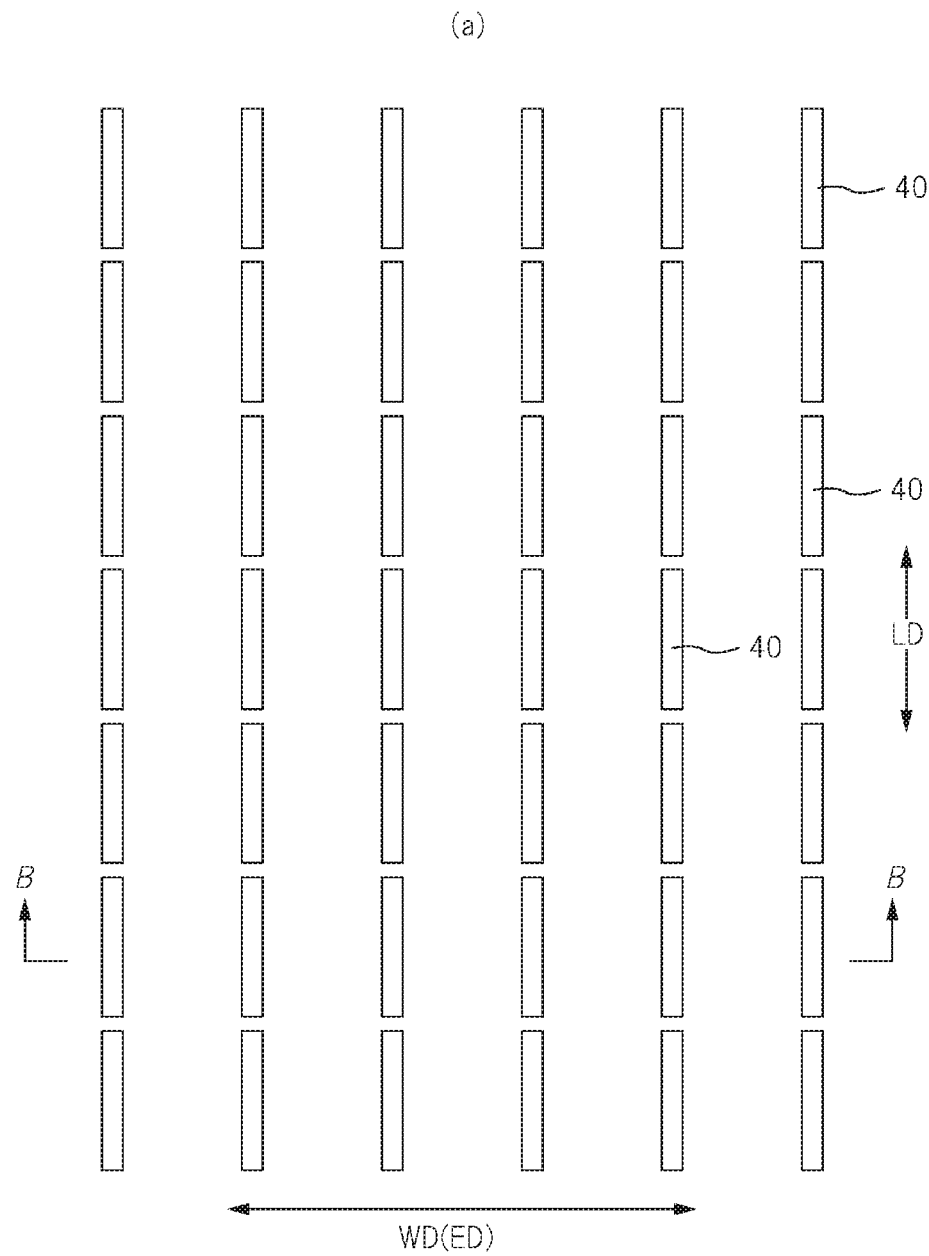
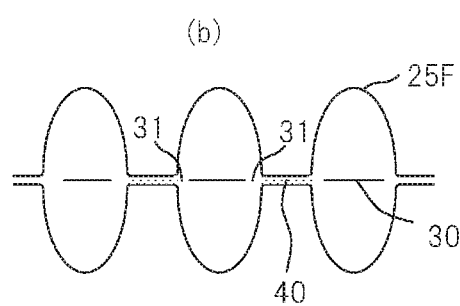

Fig.12
(a)
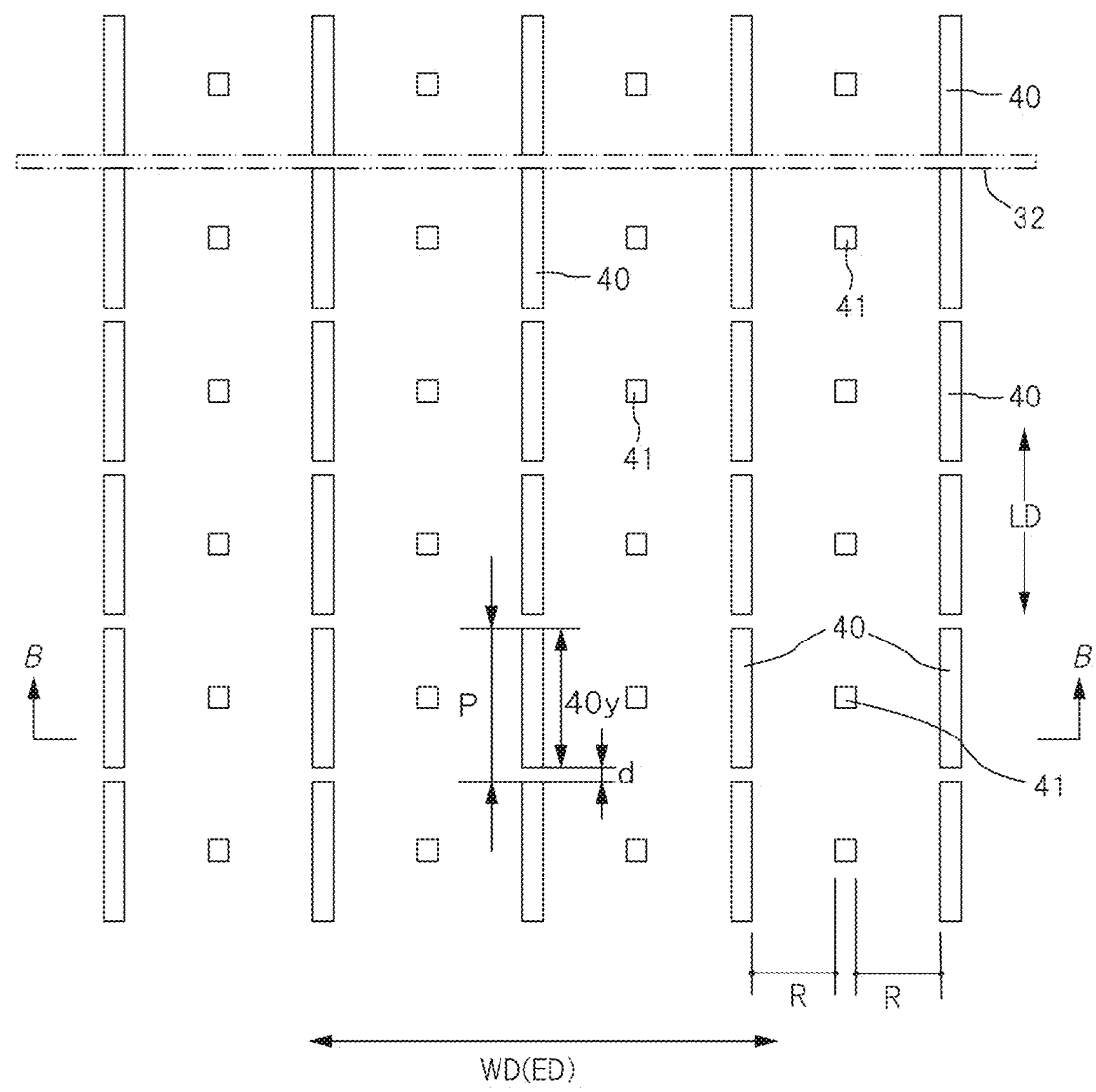
(b)
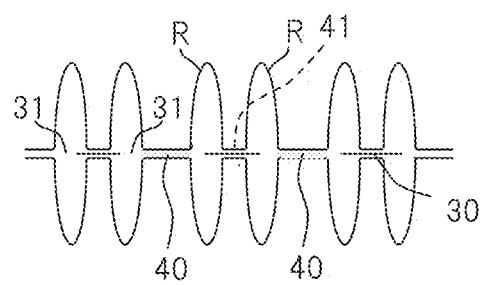

[FIG.13]
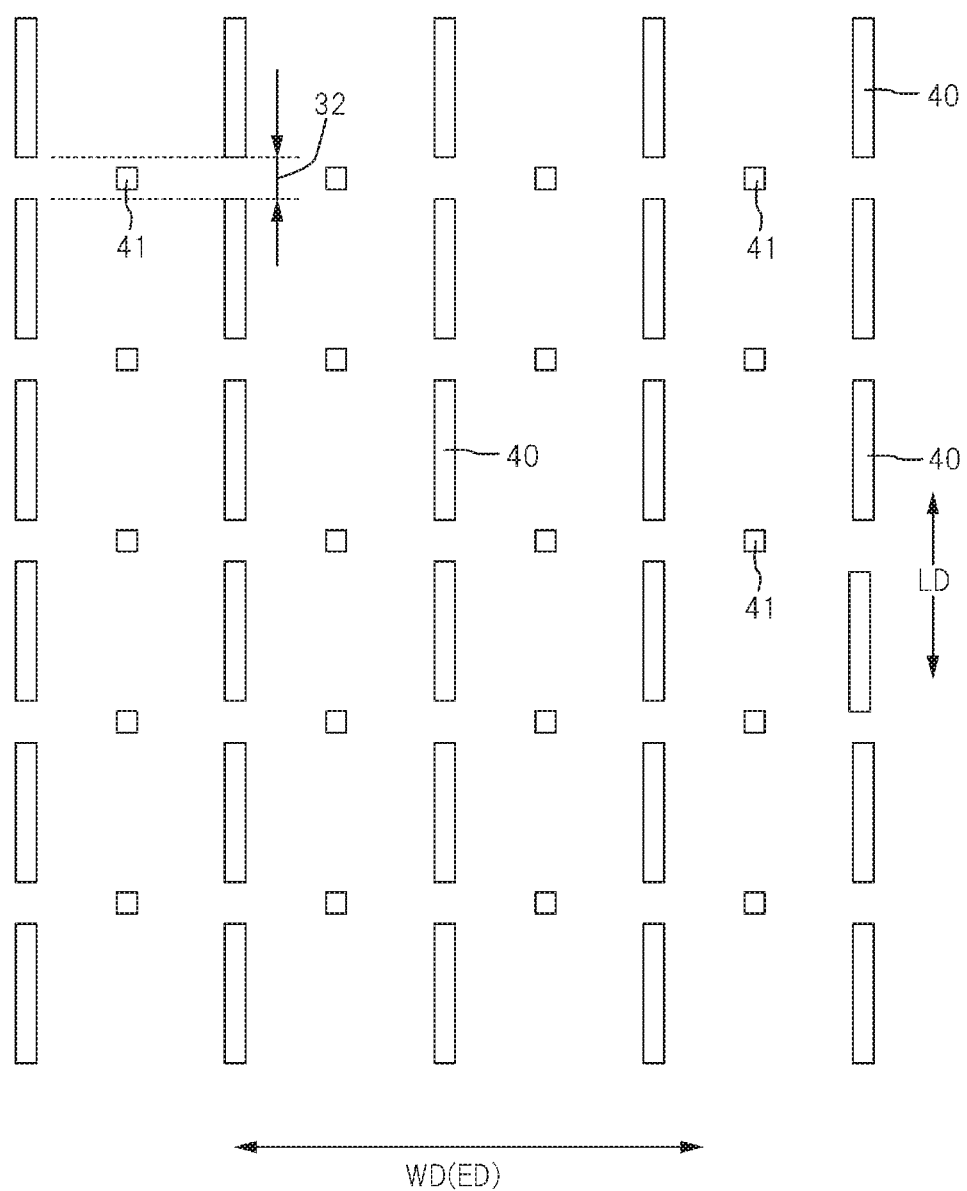

[FIG.14]
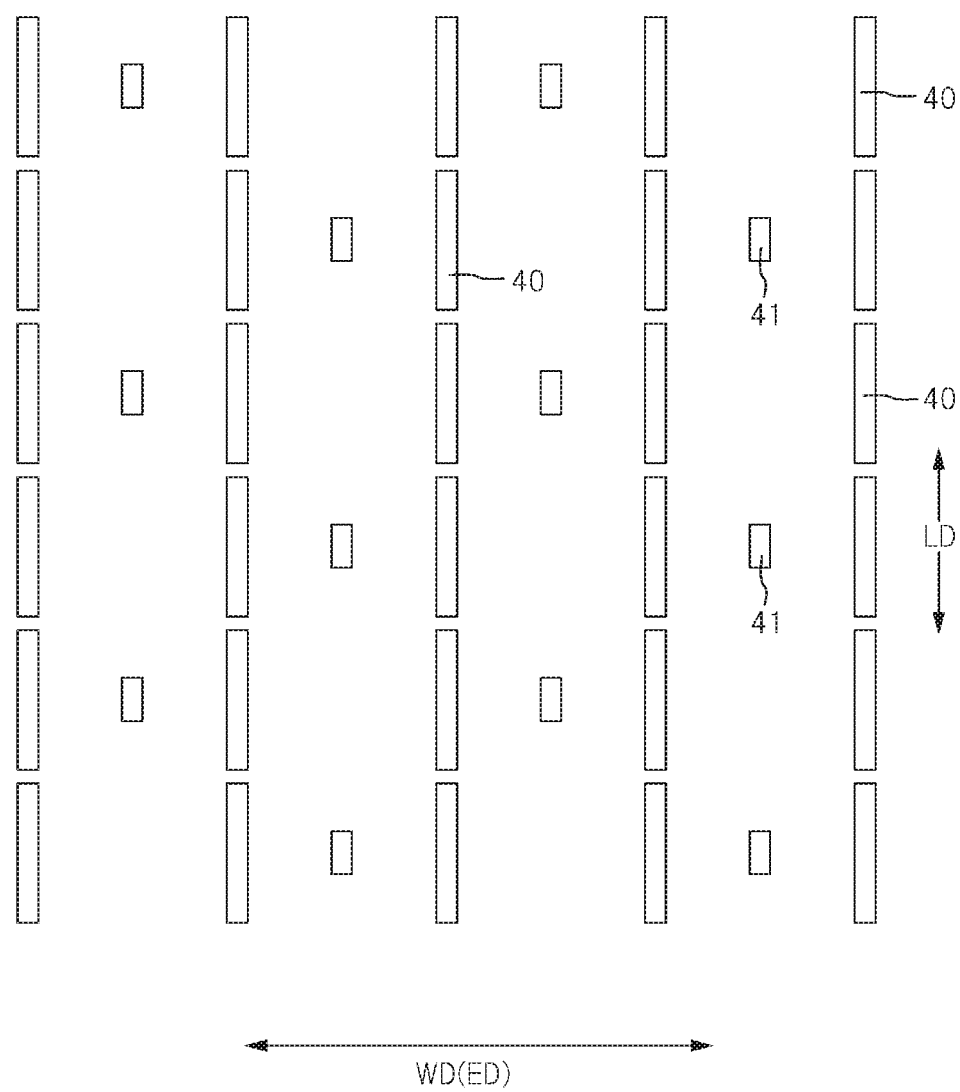

[FIG.15]
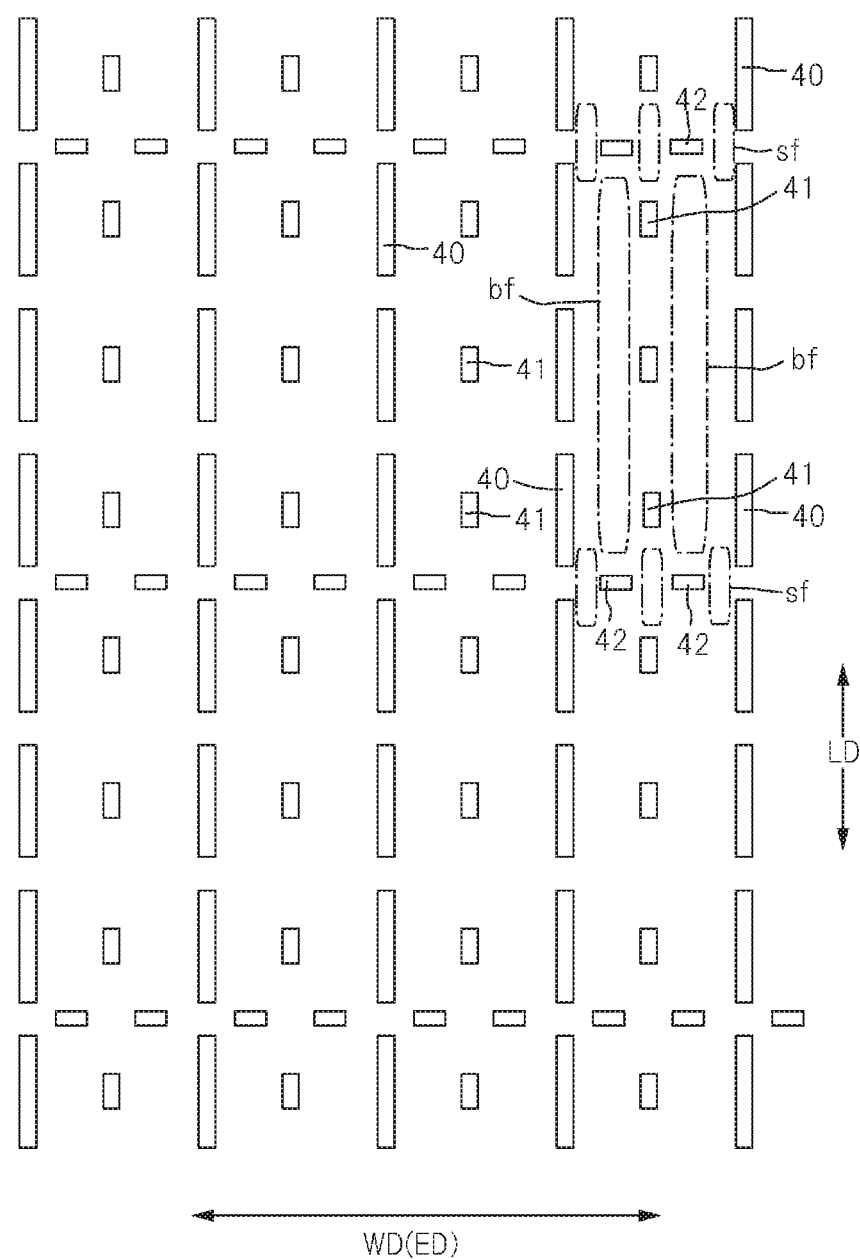

[FIG.16]
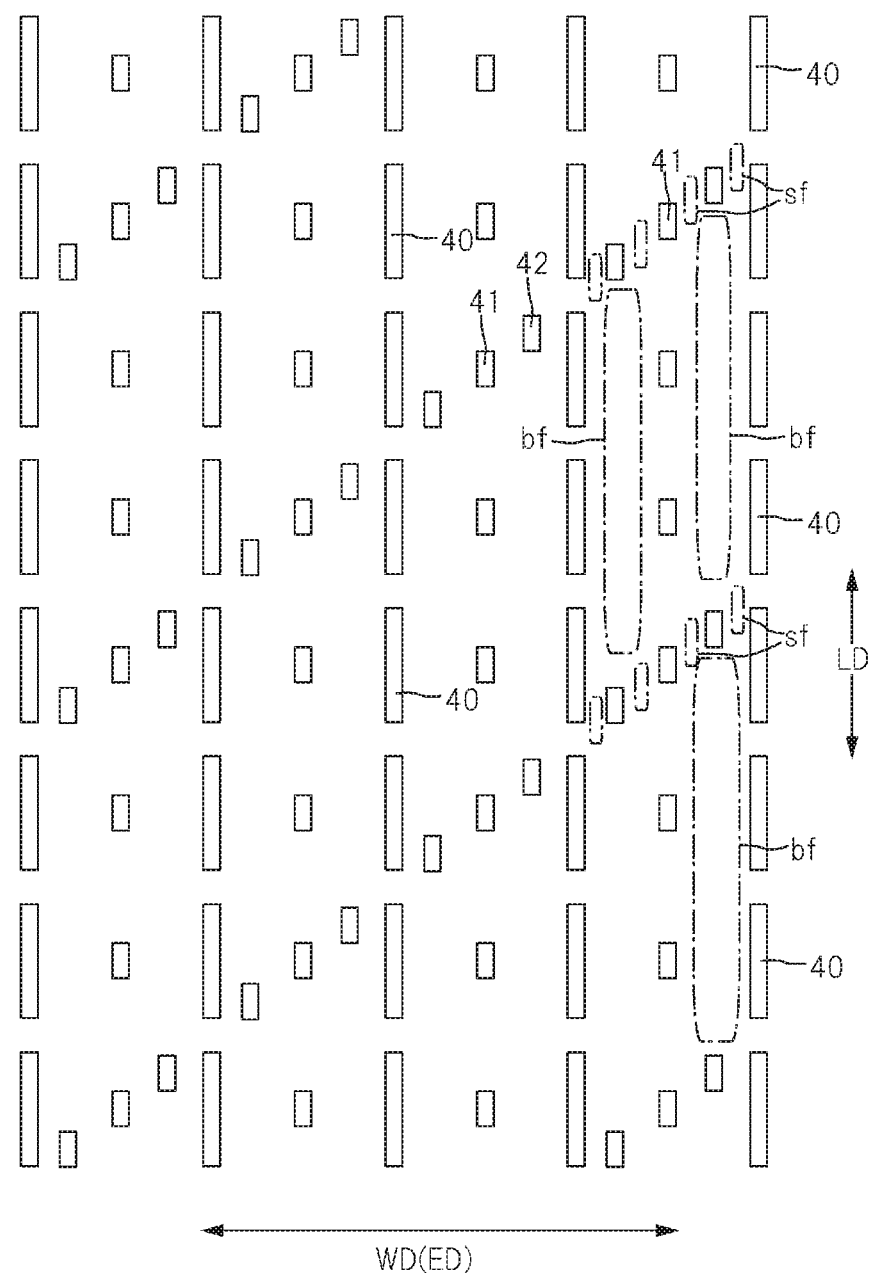

[FIG.17]
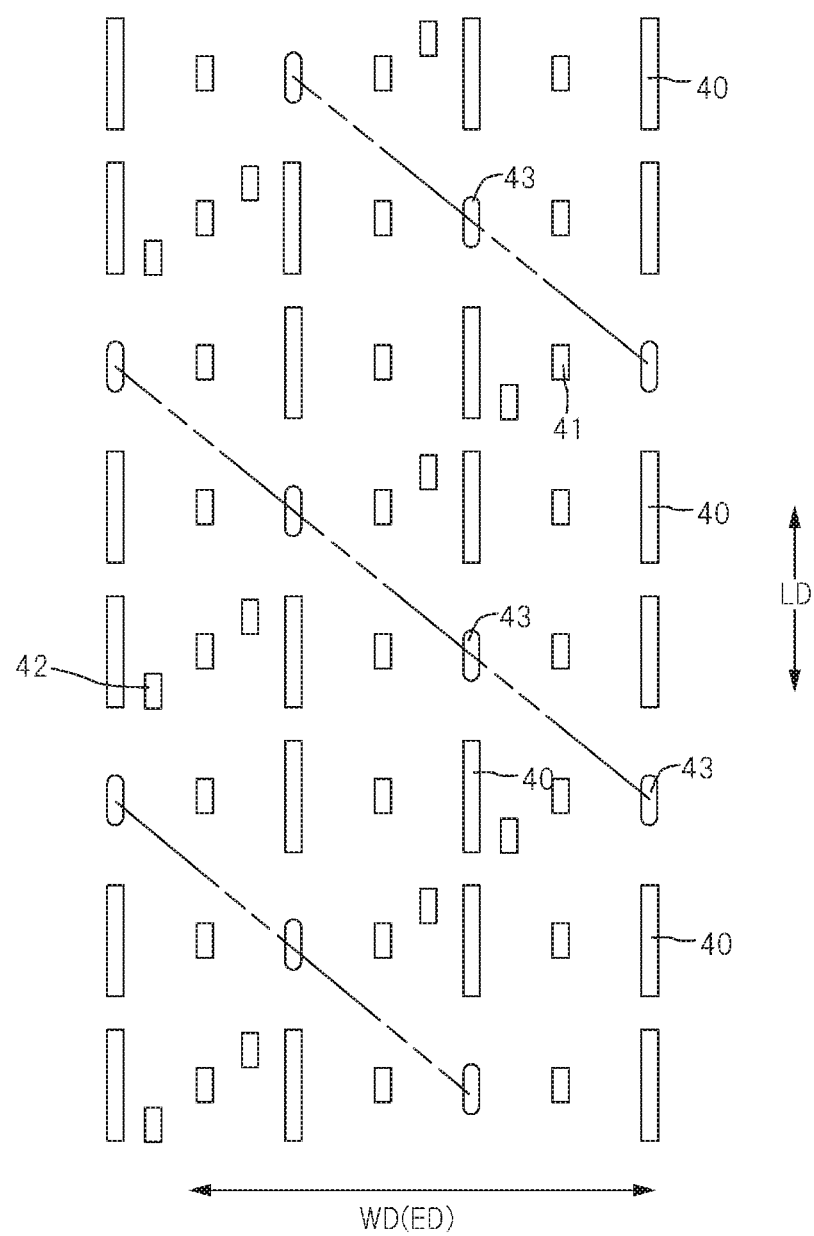

[FIG.18]
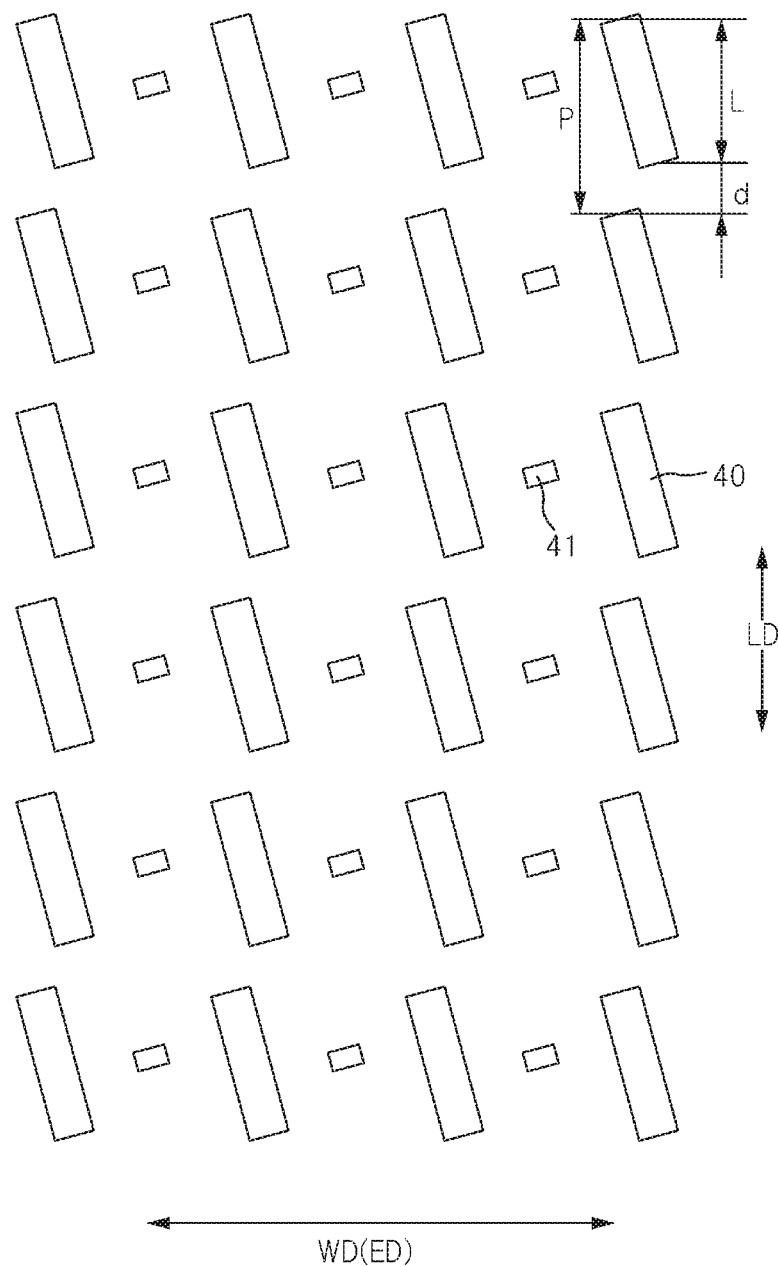

[FIG.19]
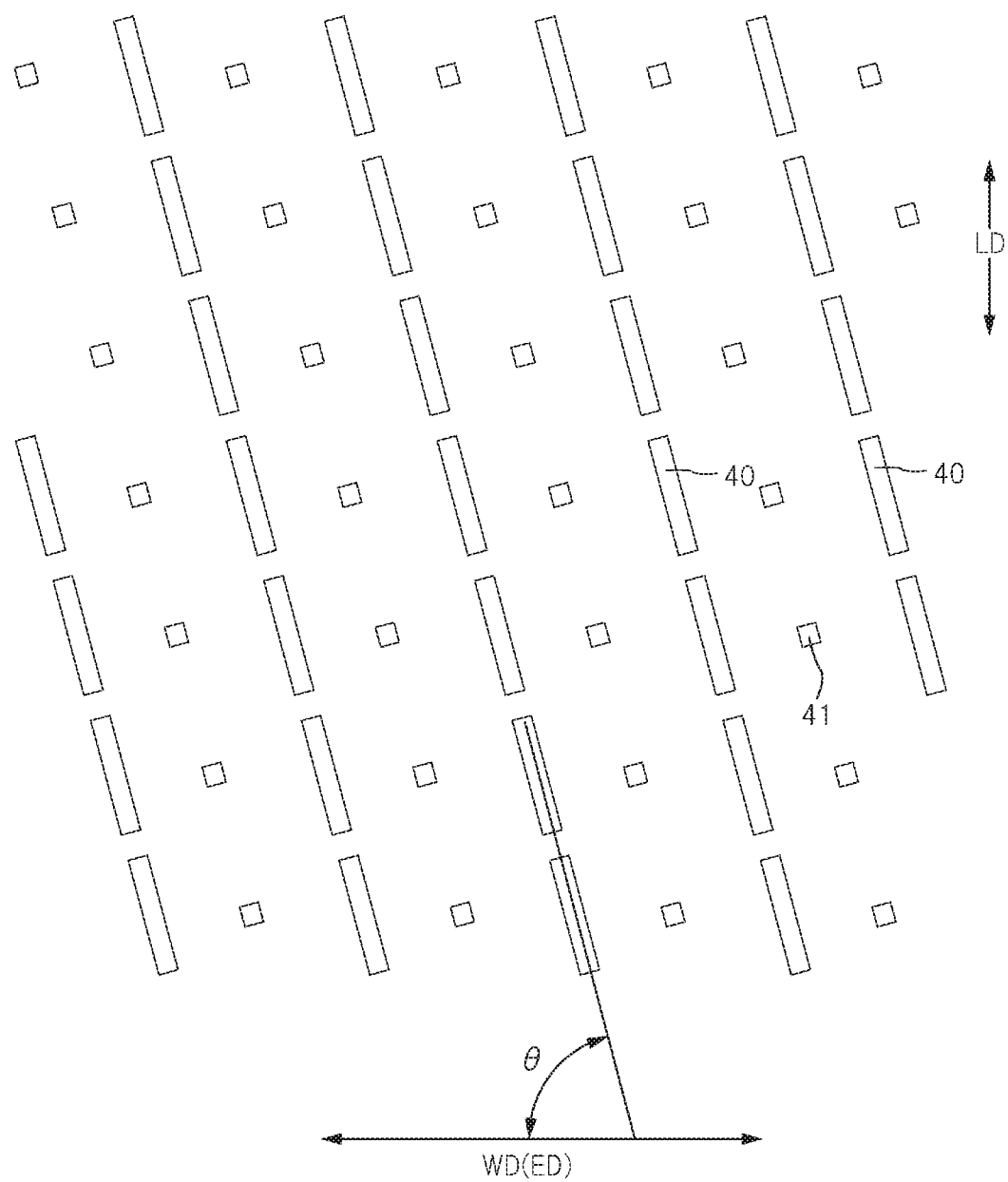

[FIG.20]
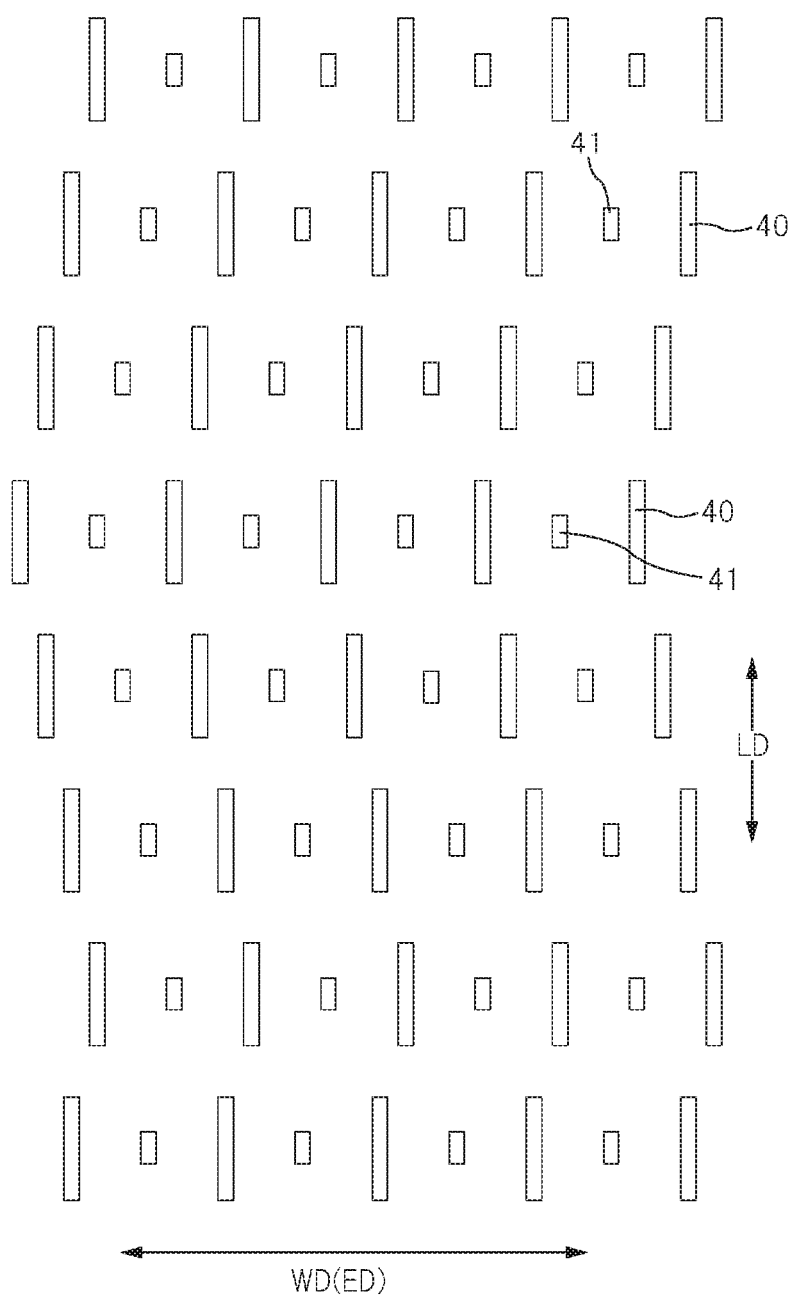

[FIG.21]
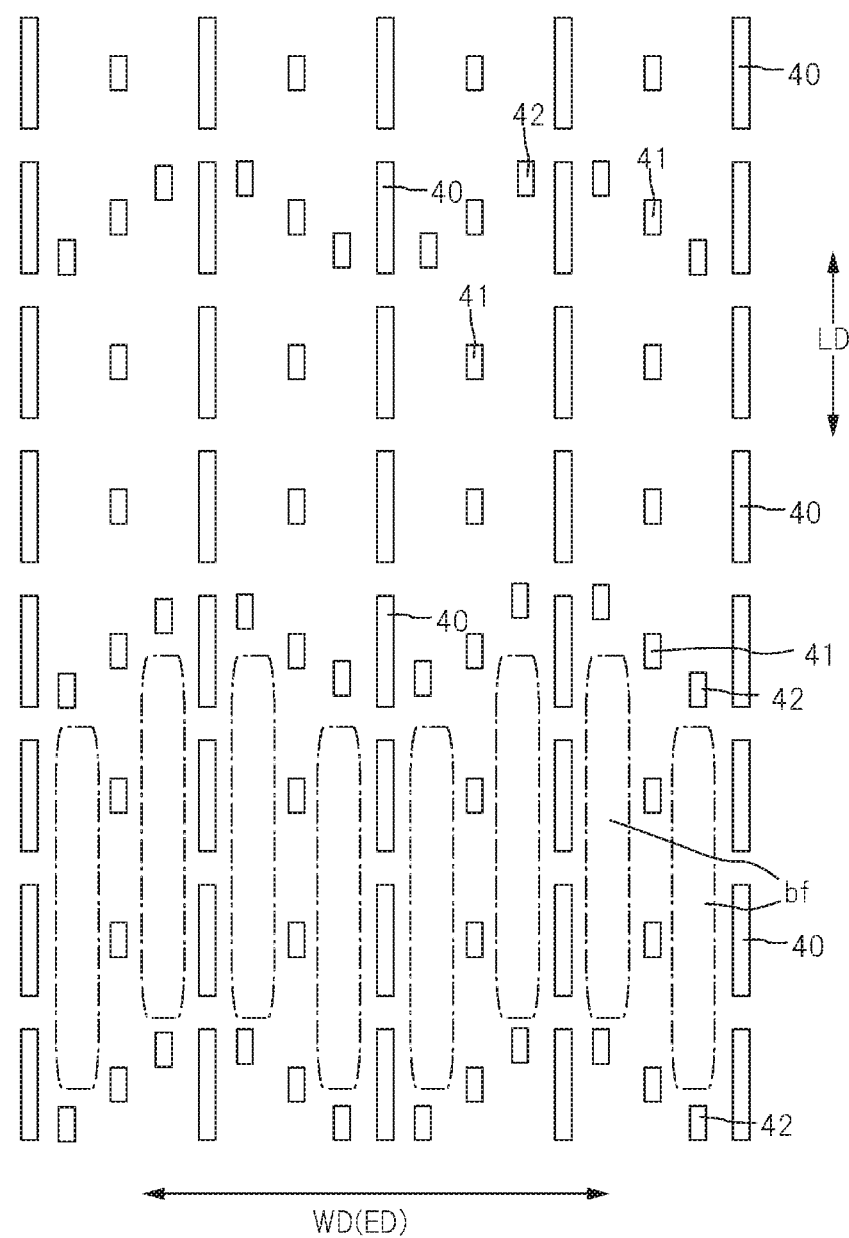

[FIG.22]
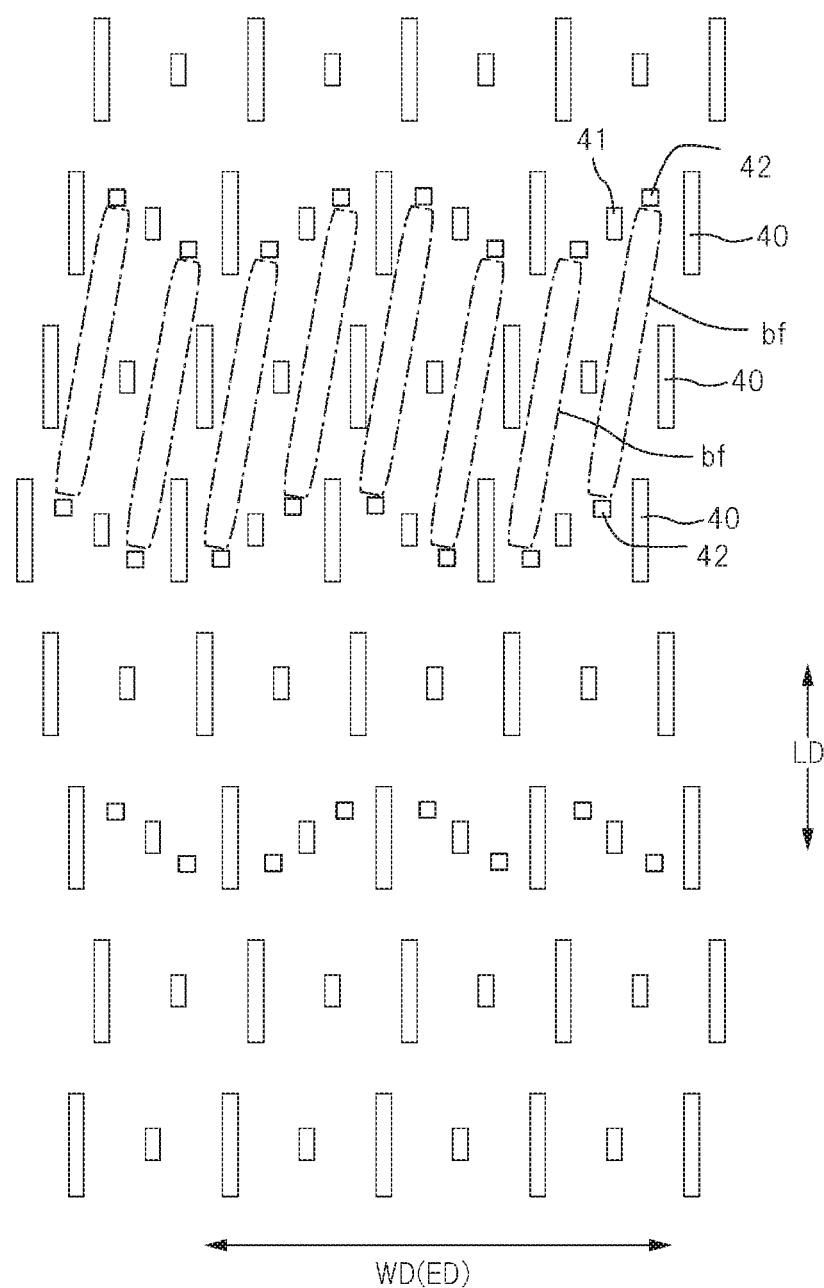

[FIG.23]
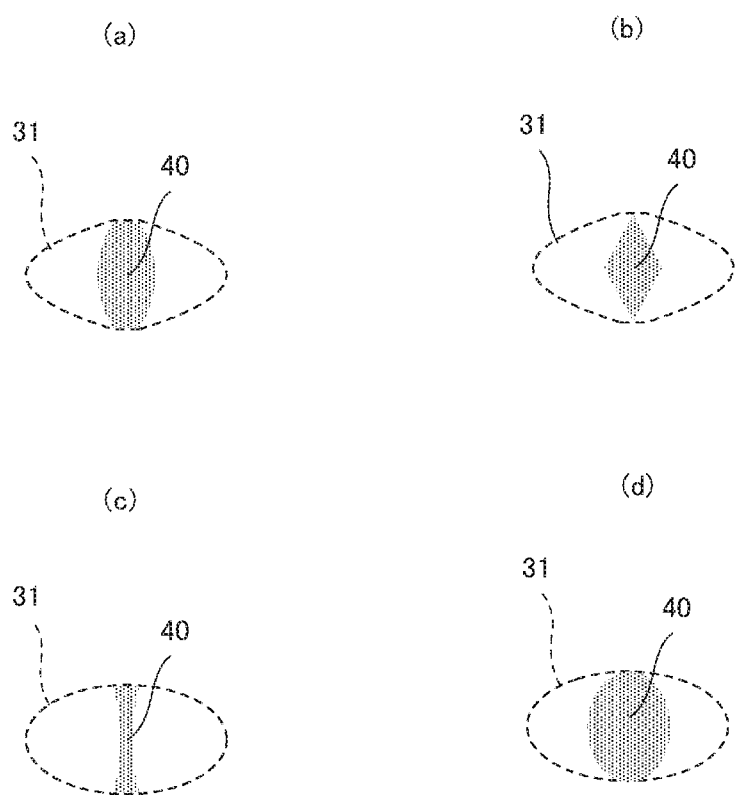

[FIG.24]
(a)
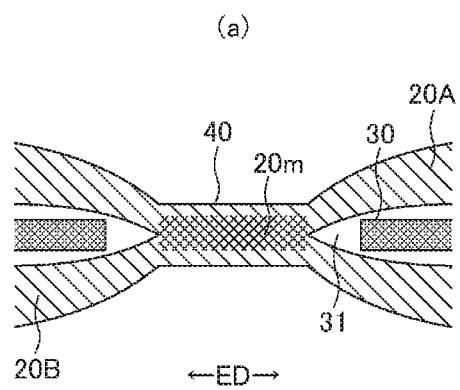
(b)
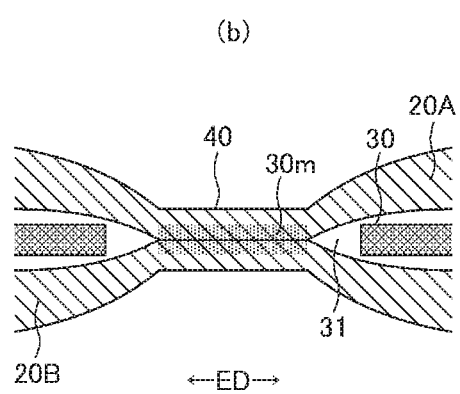
(c)
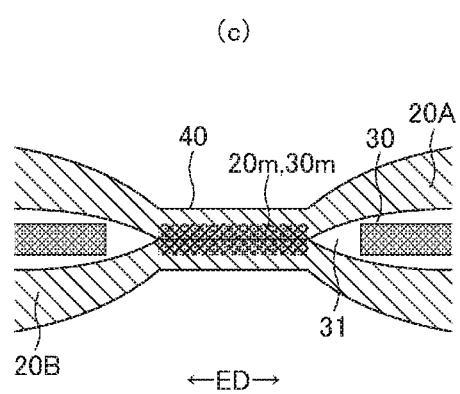

[FIG.25]
(a)
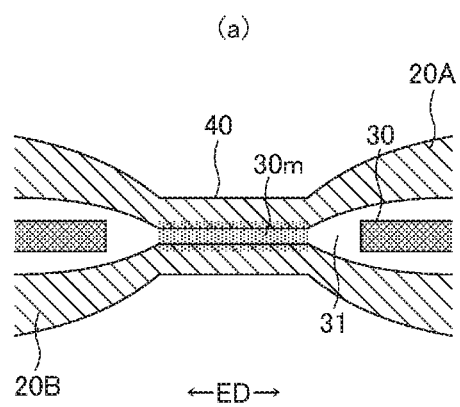
(b)
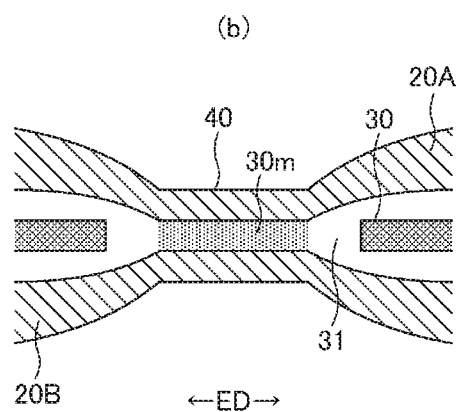
(c)
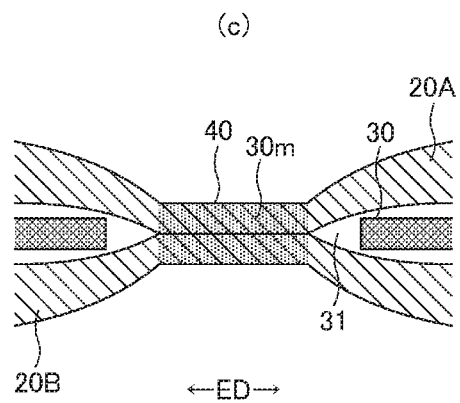

[FIG.26]
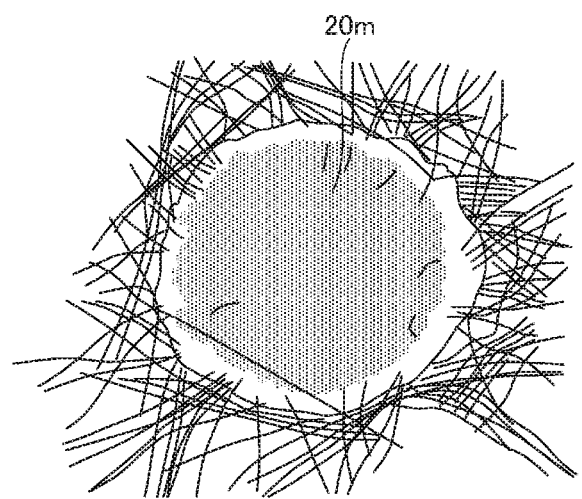
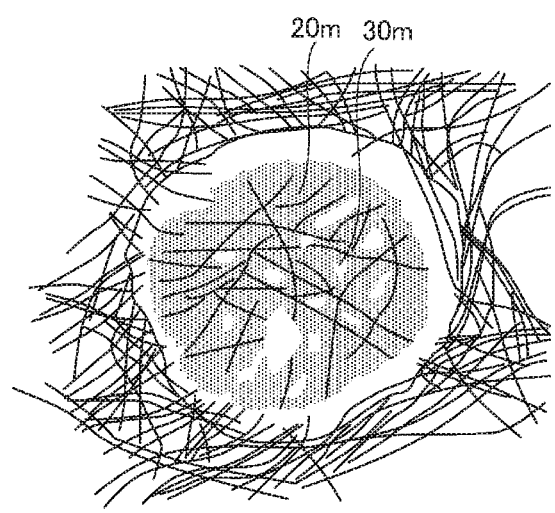
(b)

[FIG.27]
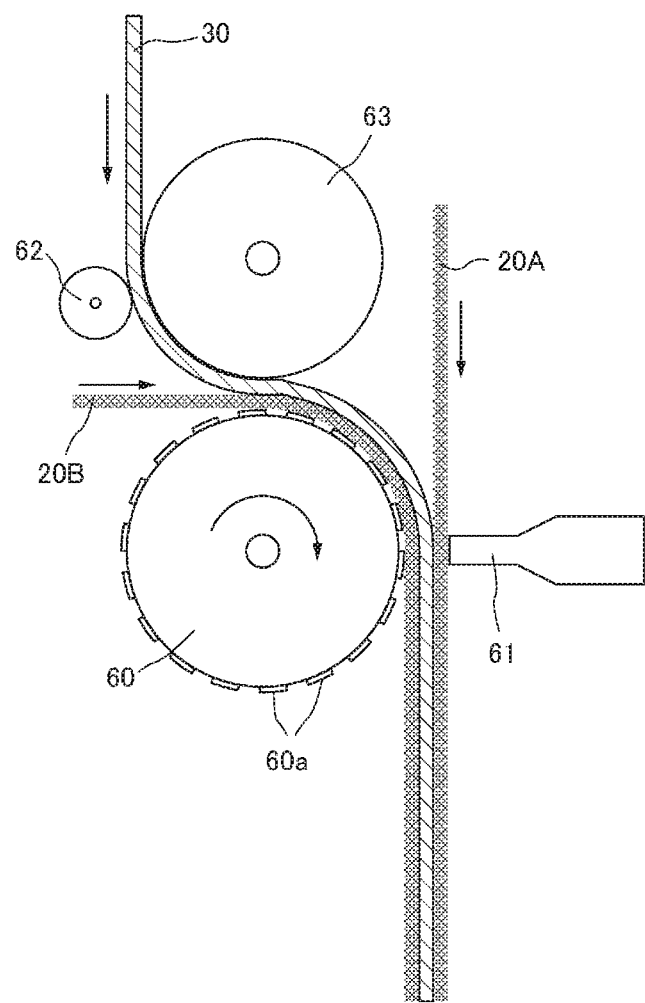

[FIG.28]
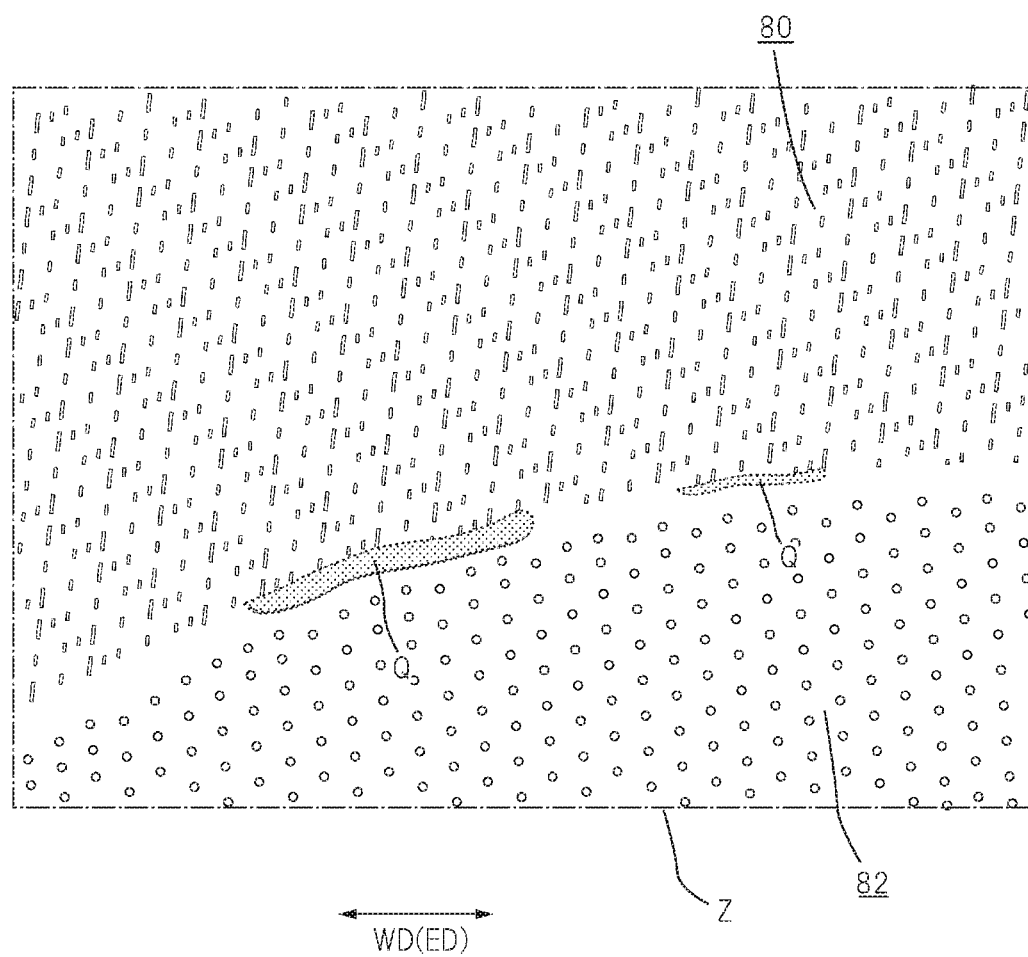

[FIG.29]
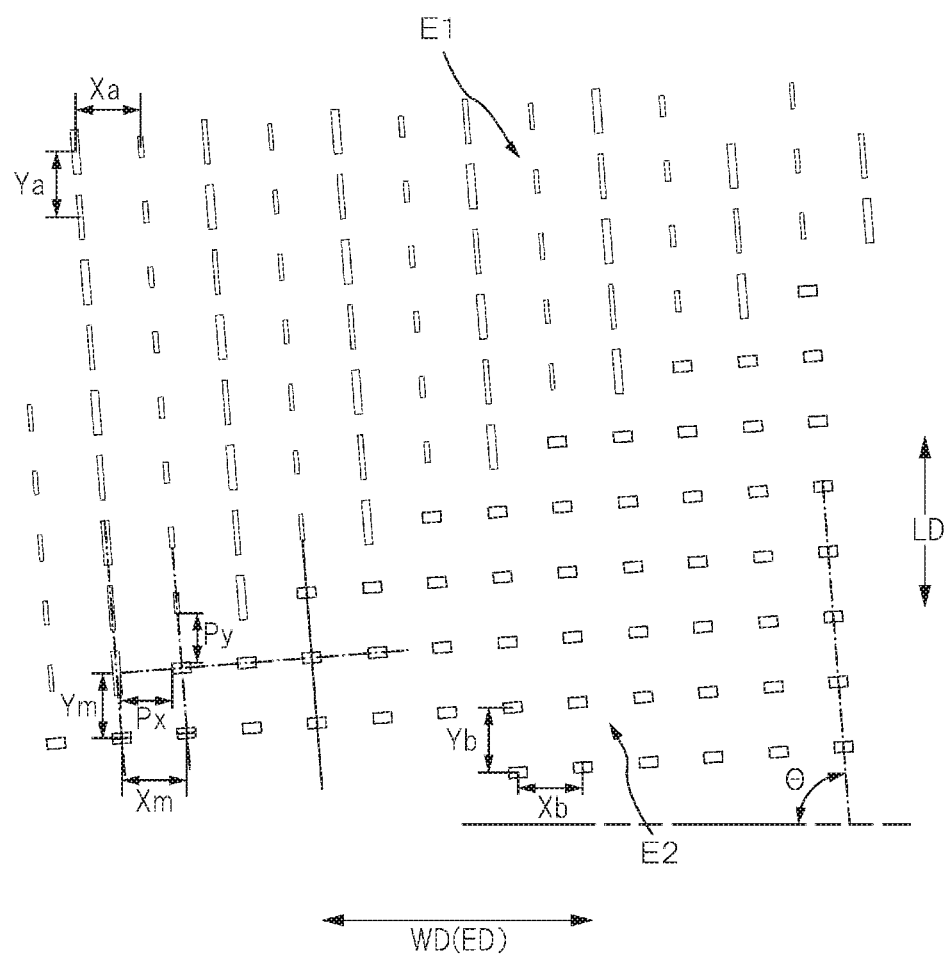

[FIG.30]
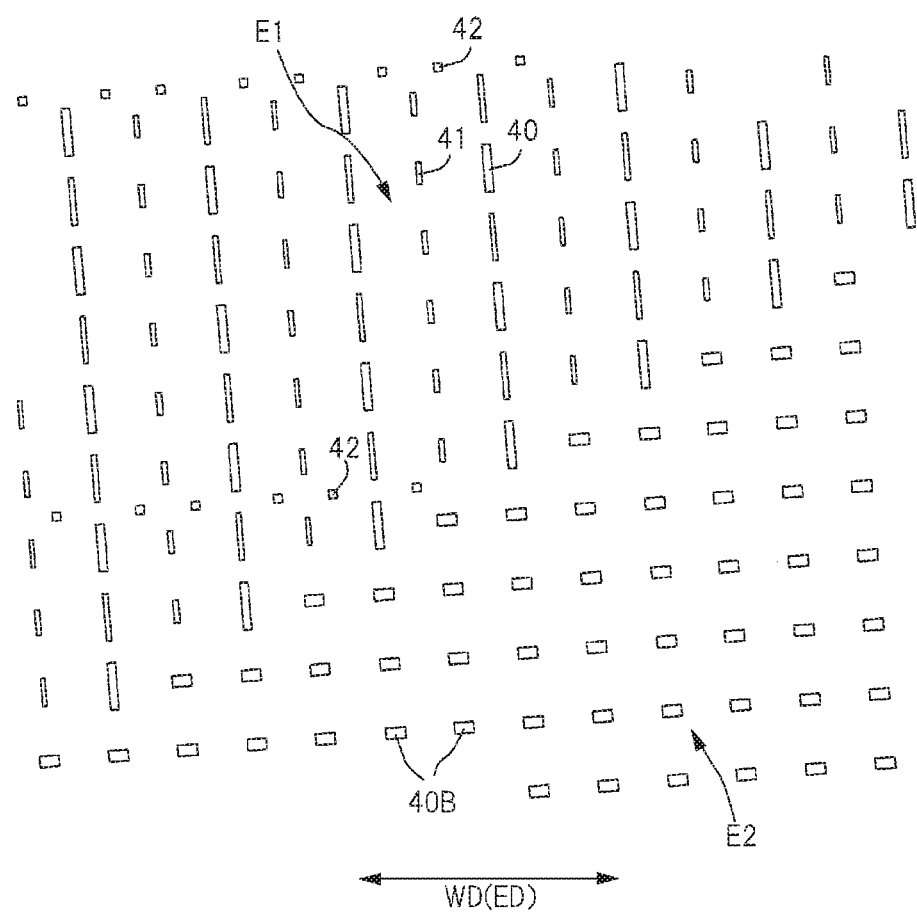

[FIG.31]
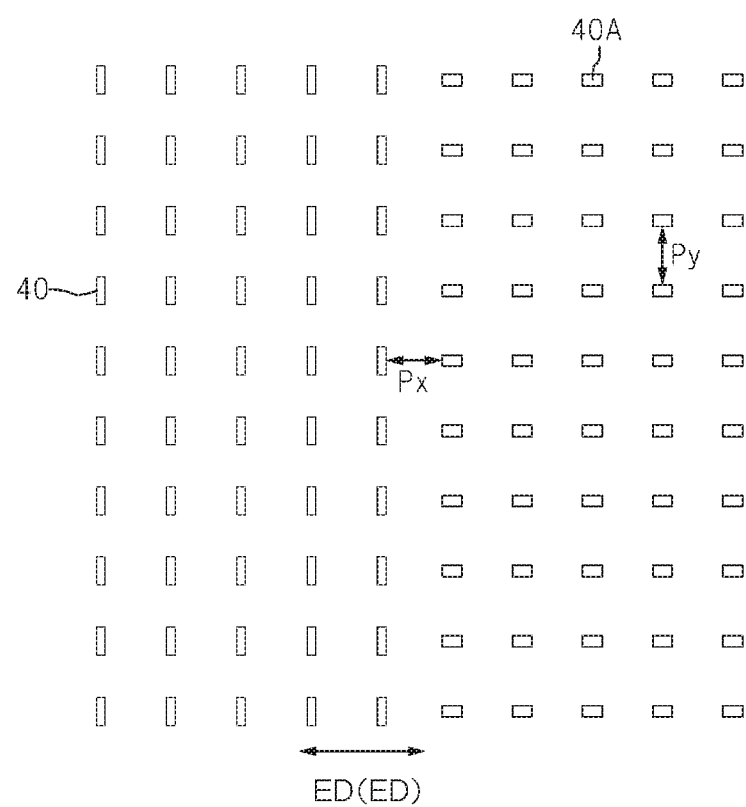

[FIG.33]
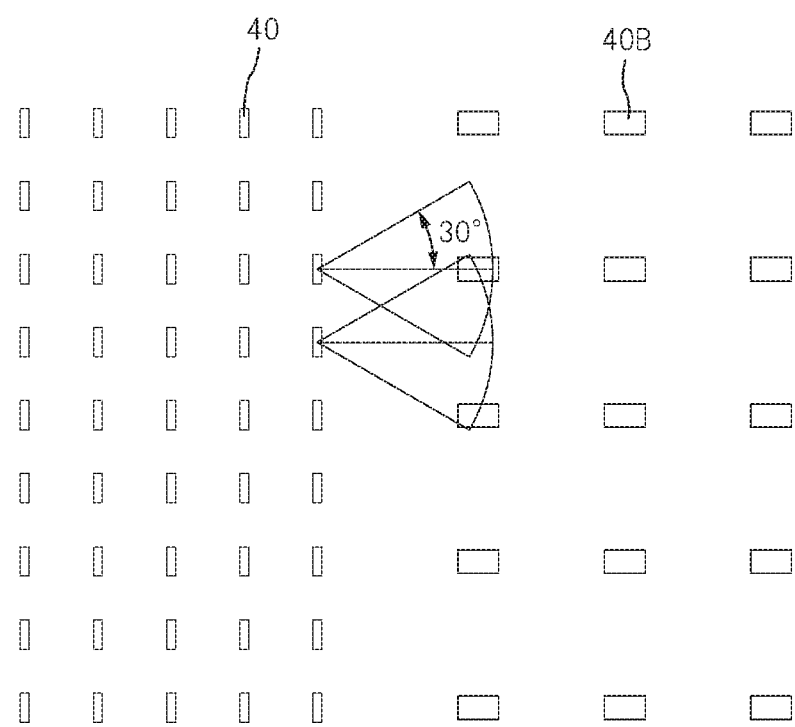

STRETCHABLE MEMBER AND DISPOSABLE WEAR ARTICLE USING STRETCHABLE MEMBER

CROSS-REFERENCE TO RELATED APPLICATIONS

This application is the U.S. national stage application of International Application PCT/JP2019/009572, filed Mar. 11, 2019, which international application was published on Sep. 26, 2019, as International Publication WO 2019/181588 in the Japanese language. The International Application claims priority of Japanese Patent Application No. 2018-051154, filed Mar. 19, 2018. The international application and Japanese application are both incorporated herein by reference, in entirety.

TECHNICAL FIELD

The present invention relates to a stretchable member having a stretchable structure in which an elastic sheet is sandwiched between a first sheet layer and a second sheet layer, and to a disposable wearing article having the stretchable member.

BACKGROUND ART

In disposable wearing articles, for example, disposable diapers, in order to improve fitting to the body surface, it is common to impart elasticity to appropriate positions such as around the legs and around the waist. Conventionally, as a technique for imparting the elasticity, a technique of attaching an elongated elastic member such as a rubber thread in a state of being stretched in the longitudinal direction thereof has been widely adopted, but when it is desired to impart the elasticity with a certain width, a form is adopted in which a rubber thread is fixed in a state of being arranged side by side at intervals in the width direction. Further, in order to obtain an article having a surface which is further excellent in fitting, a method, including the method of the present applicant, the method attaching the elastic sheet in a state of elongating in the direction of imparting the elasticity has also been proposed. (refer to, for example, Patent Literature 1)

This stretchable structure with elastic films (hereinafter also referred to as elastic sheet stretchable structure) is formed by laminating elastic films between a first sheet layer in which a stretchable region is made of a nonwoven fabric and a second sheet layer in which a stretchable region is made of a nonwoven fabric. In a state where the elastic film is elongated in the stretchable direction along surfaces of the elastic films, the first sheet layer and the second sheet layer are bonded through bonding holes penetrating the elastic film at a number of dot-like sheet bonded portions arranged at intervals in a stretchable direction and a direction orthogonal to the stretchable direction.

In such an elastic sheet stretchable structure, since an elastic film shrinks between sheet bonded portions, the intervals between the sheet bonded portions become narrow in a natural length state, and shrinkage wrinkles extending in a direction intersecting with the stretchable direction are formed between sheet bonded portions in the first sheet layer and the second sheet layer.

On the contrary, at the time of elongation, as the elastic film elongates between the sheet bonded portions, the intervals between sheet bonded portions and the shrinkage wrinkles in the first sheet layer and the second sheet layer are expanded, and the first sheet layer and the second sheet layer can elastically elongate up to a full spread state. This elastic sheet stretchable structure not only has excellent surface fitting but also has no surface bonding between the first sheet layer and the second sheet layer and the elastic film, and the bonding between the first sheet layer and the second sheet layer is extremely small, and therefore it is very flexible, and there is an advantage that bonding holes of the elastic film also contributes to improve air permeability in the thickness direction.

In Patent Literature 1, the elastic film between regions also is prevented from tearing. As a means for that purpose, a buffering stretchable portion is formed between a stretchable region and a non-stretchable region, in which the area ratio of dot-like bonded portions is lower than that of the non-stretchable region and higher than that of the main stretchable portion. That is, it is presupposed that there is a non-stretchable region.

CITATION LIST

Patent Literature

Patent Literature 1: JP 5967736 B2
Patent Literature 2: JP 2015-204982 A
However, it has been found that the elastic film may be torn even between the stretchable regions.

SUMMARY OF INVENTION

Technical Problem

Therefore, a main object of the present invention is to prevent or suppress the occurrence of tearing of an elastic film between stretchable regions in an elastic sheet stretchable structure.

Solution to Problem

A stretchable member of the present invention that has solved the above-described problem includes
  an elastic sheet stretchable structure in which an elastic sheet is interposed between a first sheet layer having air permeability and a second sheet layer having air permeability, and the first sheet layer and the second sheet layer are bonded at a large number of fused dot-like bonded portions arranged at intervals.
  A stretchable region having the elastic sheet stretchable structure can be expanded and contracted in a stretchable direction due to a contraction force of the elastic sheet,
    the stretchable region has at least two stretchable regions including a first stretchable region and a second stretchable region, in which at least one of an arrangement pattern of the bonded portion and a shape of the bonded portion is different, and
    at a boundary between the first stretchable region and the second stretchable region, a separation distance in an elastic limit elongation state between a bonded portion located on a side of the boundary of the first stretchable region in the stretchable direction and a bonded portion located on a side of the boundary of the second stretchable region in the stretchable direction is 10 mm or less.
  The elastic sheet may be an elastic nonwoven fabric or the like in addition to an elastic elastomer film.
  At the boundary between the first stretchable region and the second stretchable region, when a separation distance in an elastic limit elongation state between a bonded portion located on the side of the boundary of the first stretchable region in a stretchable direction and a bonded portion located on the side of the boundary of the second stretchable region in a stretchable direction is 10 mm or less, tearing of an elastic film can be prevented or suppressed.

For example, it is conceivable that side portions and leg around portions of an underpants-type disposable diaper are a stretchable region, for example, the elastic limit elongation of the stretchable region of the side portions is large, and the elastic limit elongation of the stretchable region of the leg around portion is small.

In this case, it is conceivable that, between the stretchable region on the side portion and the stretchable region of the leg around portion, the arrangement pattern of the bonded portion and the shape of the bonded portion are made different, and the stretchable regions are separated from each other considering design.

However, it has been found that when a separation distance in the elastic limit elongation state between the bonded portion located on the side of the boundary of the first stretchable region in a stretchable direction and the bonded portion located on the side of the boundary of the second stretchable region in a stretchable direction is 15 mm or more, the elastic film may be torn between the stretchable regions.

The cause of this tearing is considered as follows, for example.

In the stretchable region, the elastic film is bonded at a large number of fused dot-like bonded portions, but at the time of the fusion bonding, the elastic film is considerably thermally damaged. It is considered that there is difference in damage between the stretchable region and the boundary region where is not thermally damaged, and when a product, for example, an underpants-type disposable diaper, is stretched in a width direction for wearing, the elastic film reaches the limit of the stress resistance at the boundary portion of the stretchable region where the difference in damage occurs, and the elastic film is torn.

In the process of commercialization, if an actual machine test is performed, tearing sites are not scattered in the stretchable region, but the elastic film tears mainly at the boundary portion. Therefore, the cause of the tearing is considered to be the above reason.

On the other hand, it is considered that, when the separation distance is 10 mm or less according to the present invention, the difference with the width direction pitch of the bonded portion in the stretchable region (a range of 1 to 10 mm is desirable) is small, when the stretchable region is stretched in a width direction, the strain due to stretching causes deformation of the film so as to be absorbed when a through hole is formed in each bonded portion. Since this deformation of the film is dispersed in the respective bonded portions of the first stretchable region and the second stretchable region, the difference in thermal damage does not become apparent between the first stretchable region and the second stretchable region, and consequently tearing of the elastic film is prevented or suppressed.

When the above-described conventional elastic sheet stretchable structure is adopted, a stretching stress in a width direction is increased, and for example, in the case of applying to an underpants-type disposable diaper, some wearers might be tightened too strongly. Therefore, it is desired to provide a material which has low stretching stress in a stretchable direction, and which is excellent in wearing feeling when applied to an absorbent article.

For this purpose, it is desirable that at least one of the arrangement patterns of the first stretchable region and the second stretchable region be an arrangement pattern in which rows of bonded portions are formed at intervals along an alignment direction which intersects with a stretchable direction at an angle of a range of 30 to 150° (not including 90°).

In such a stretchable structure, the stretching stress in the stretchable direction is low. Moreover, shrinking wrinkles extending in an alignment direction (orthogonal direction) intersecting the stretchable direction are formed between bonded portion rows in a preferable form.

This will be further described later with an embodiment.

In comparison between the first stretchable region and the second stretchable region, arrangement patterns of the bonded portions are the same, but shapes of the bonded portions may be different. In this case, "shapes of bonded portions are different" means "external shapes of bonded portions" are different, and also "external shapes of bonded portions" are the same, but directions are different.

As a result, from the viewpoint of appearance, the difference in the bonded portion design group between the first stretchable region and the second stretchable region can be appealed to consumers.

For example, the customers can have an image that side portions of an underpants-type disposable diaper is regarded as the first stretchable region, and leg around portions are regarded as the second stretchable region, and the elastic limit elongation is large at the side portion of the first stretchable region to fit softly to a wearer, and the elastic limit elongation is small in the leg around portions of the second stretchable region to fit tightly around the leg area.

When at least one of the arrangement patterns of the first stretchable region and the second stretchable region is formed by a plurality of bonded portions having different shapes, it can appeal to consumers with a complicated design.

A form having an intermediate stretchable region between the first stretchable region and the second stretchable region can be applied. This form is as follows.

An elastic sheet stretchable structure is provided in which an elastic sheet is interposed between a first sheet layer having air permeability and a second sheet layer having air permeability, and the first sheet layer and the second sheet layer are bonded at a large number of fused dot-like bonded portions arranged at intervals.

A stretchable region having the elastic sheet stretchable structure can be expanded and contracted in a stretchable direction due to a contraction force of the elastic sheet, the stretchable region has a first stretchable region and a second stretchable region, in which at least one of an arrangement pattern of the bonded portion and a shape of the bonded portion is different, an intermediate stretchable region is provided between the first stretchable region, in a case where (1) a pitch of the bonded portions in the intermediate stretchable region in a stretchable direction is Xm, (2) a pitch of the bonded portions in the first stretchable region in a stretchable direction is Xa, and (3) a pitch of the bonded portions in the second stretchable region in a stretchable direction is Xb, $Xm \leq \{(Xa+Xb)/2\} \times 1.6$ is established, a separation distance in an elastic limit elongation state between a bonded portion located on a side of the first stretchable region in the stretchable direction of the intermediate stretchable region and a bonded portion located on a side of the intermediate stretchable region of the first stretchable region is 10 mm or less, and a separation distance in an elastic limit elongation state between a bonded portion located on a side of the second stretchable region in the stretchable direction of the intermediate stretchable region and a bonded portion located on a side of the intermediate stretchable region of the second stretchable region is 10 mm or less.

Further, in the case where
(1) a pitch of the bonded portions in an orthogonal direction orthogonal to a stretchable direction of the intermediate stretchable region is Ym,
(2) a pitch of the bonded portions in an orthogonal direction of the first stretchable region is Ya, and
(3) a pitch of the bonded portions in an orthogonal direction of the second stretchable region is Yb,
Ym≤{(Ya+Yb)/2}×1.6 is established.

In the above-described form, it is possible that at least one of the arrangement patterns of the first stretchable region and the second stretchable region is an arrangement pattern in which rows of bonded portions are formed at intervals along an alignment direction which intersects with a stretchable direction at an angle of a range of 30 to 150° (not including 90°).

The reason why tearing of the elastic film is prevented or suppressed in the form having the intermediate stretchable region between the first stretchable region and the second stretchable region is considered as follows.

That is, it is considered that, when Xm≤{(Xa+Xb)/2}×1.6 is established, between the first stretchable region and the intermediate stretchable region, and between the intermediate stretchable region and the second stretchable region, the change in the pitch in a width direction of the bonded portion is small, when the bonded portion is stretched in the width direction, the strain due to the stretching causes deformation of a film so as to be absorbed when through holes are formed in each bonded portion. Since this deformation of the film is dispersed at each bonded portion of the first stretchable region and the second stretchable region, the difference in thermal damage does not become apparent, and consequently tearing of the elastic film is prevented or suppressed.

An underpants-type disposable wearing article having the stretchable member and including an outer body integrally provided from a front body to a back body or an outer body separately provided on the front body and the back body, an inner body attached to an intermediate portion in a width direction of the outer body and provided over both front and back sides of a crotch portion, a side seal portion in which both side portions of the outer body in the front body and both side portions of the outer body in the back body are bonded respectively, a waist opening, and a pair of right and left leg openings.

The outer body in at least one of the front body and the back body extends over at least a width direction range corresponding to between the side seal portions in a part of a range in a front-back direction, and the elastic sheet stretchable structure is provided such that the stretchable direction of the stretchable region is arranged in the width direction.

In the elastic sheet stretchable structure of the present invention, a stretching stress in a stretchable direction is low. Moreover, shrinking wrinkles extending in an alignment direction (orthogonal direction) intersecting the stretchable direction are formed between the first bonded portion rows in a preferable form.

This will be further described later with an embodiment.

It is desirable that a large number of second bonded portion rows in which the second bonded portions are provided at intervals in an alignment direction be formed between the first bonded portion rows.

When the second bonded portion rows are formed, shrinking wrinkles are repeated in an alignment direction in the second bonded portion rows, such that the appearance is excellent in aesthetic appearance.

Further, it is more preferable that bonded portions having a length of the first bonded portion and bonded portions having a length longer than that of the first bonded portion are not formed in the second bonded portion rows.

If a bonded portion having a length equal to or longer than that of the first bonded portion is formed in the second bonded portion row, a stretching stress in the stretchable direction is low, and the length range of the bonded portion becomes a wrinkle non-formation range, which causes deterioration of the appearance.

On the other hand, if such a bonded portion is not formed, the stretching stress in the stretchable direction is low, and shrinking wrinkles having a sufficient length in an alignment direction are formed. Therefore, a stretchable member or absorbent article which is flexible and having excellent appearance can be strongly appealed.

The stretchable member according to the present invention can be incorporated as a member of a disposable wearing article.

Advantageous Effects of Invention

As described above, according to the present invention, in the elastic sheet stretchable structure, the stretching stress in the stretchable direction is low, and when the stretchable member is applied to a disposable wearing article, wearing feeling is improved.

BRIEF DESCRIPTION OF DRAWINGS

FIG. 10 is a plan view illustrating a bonded portion arrangement disclosed in Patent Literature 2.
FIG. 11 is a plan view illustrating a bonded portion arrangement as a reference example for explanation.
FIG. 12(a) is a plan view,
and FIG. 12(b) is a cross-sectional view taken along line B-B, illustrating a first embodiment of a bonded portion arrangement according to the present invention.

FIG. 13 is a plan view illustrating a second embodiment of a bonded portion arrangement according to the present invention.

FIG. 14 is a plan view illustrating a third embodiment of a bonded portion arrangement according to the present invention.

FIG. 15 is a plan view illustrating a fourth embodiment of a bonded portion arrangement according to the present invention.

FIG. 16 is a plan view illustrating a fifth embodiment of a bonded portion arrangement according to the present invention.

FIG. 17 is a plan view illustrating a sixth embodiment of a bonded portion arrangement according to the present invention.

FIG. 18 is a plan view illustrating a seventh embodiment of a bonded portion arrangement according to the present invention.

FIG. 19 is a plan view illustrating an eighth embodiment of a bonded portion arrangement according to the present invention.

FIG. 20 is a plan view illustrating a ninth embodiment of a bonded portion arrangement according to the present invention.

FIG. 21 is a plan view illustrating a tenth embodiment of a bonded portion arrangement according to the present invention.

FIG. 22 is a plan view illustrating an eleventh embodiment of a bonded portion arrangement according to the present invention.

FIG. 23 is a plan view illustrating the shape of a bonded portion according to the present invention.

FIG. 24 is a cross-sectional view illustrating an example of a bonding form at a bonded portion according to the present invention.

FIG. 25 is an explanatory cross-sectional view illustrating an example of a bonding form.

FIG. 26 is a plan view illustrating a bonding form example.

FIG. 27 is a schematic view of an ultrasonic sealing device for manufacturing a stretchable member.

FIG. 28 is an explanatory view of an example of a tearing point of an elastic film.

FIG. 29 is a plan view of an example of a stretchable region according to the present invention.

FIG. 30 is a plan view of a second example of a stretchable region according to the present invention.

FIG. 31 is a plan view of a third example of a stretchable region according to the present invention.

FIG. 33 is a plan view of a fifth example of a stretchable region according to the present invention.

DESCRIPTION OF EMBODIMENTS

Figure 1:
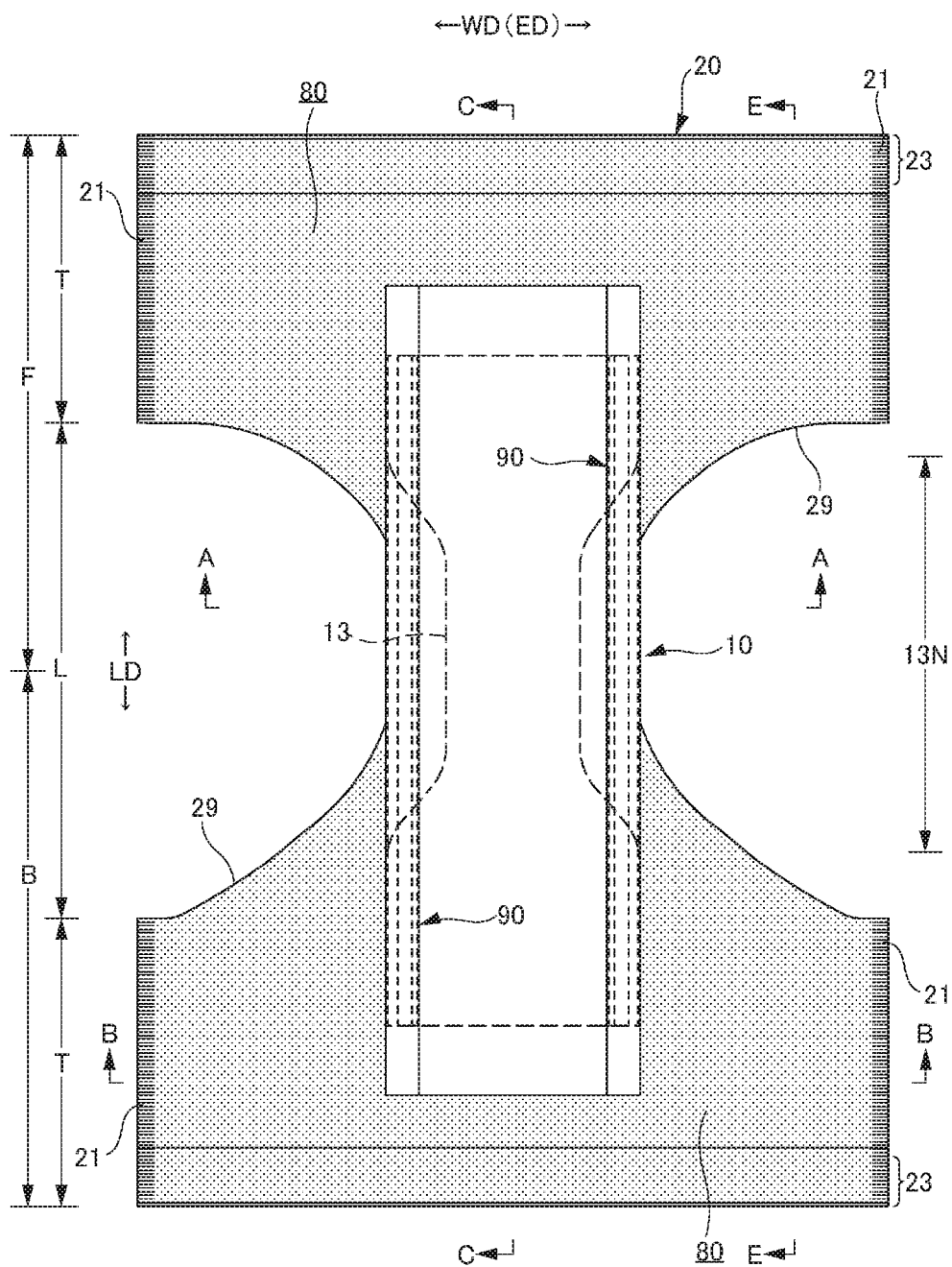
FIG. 1 is a plan view (internal surface side) of an underpants-type disposable diaper in a spread state.

Hereinafter, embodiments of the present invention will be described in detail with reference to the accompanying drawings. In addition, a dotted pattern portion in the cross-sectional view indicates a bonding means such as a hot melt adhesive.

FIGS. 1 to 6 illustrate an underpants-type disposable diaper as an example of the disposable wearing article of the present invention. The reference character LD (vertical direction) indicates a front-back direction, and WD indicates a width direction.

This underpants-type disposable diaper (hereinafter also simply referred to as a diaper) has an outer member 20 forming a front body F and a back body B, and an inner member 10 fixed to an inner surface of the outer member 20 and integrated with the outer member 20, and the inner member 10 is formed by interposing an absorber 13 between a liquid pervious top sheet 11 and a liquid impervious sheet 12. Upon manufacturing, after a back surface of the inner member 10 is bonded to an inner surface (upper surface) of the outer member 20 by a bonding means such as a hot melt adhesive, the inner member 10 and the outer member 20 are folded at the center in the front-back direction LD (longitudinal direction) which is a boundary between the front body F and the back body B, and both side portions thereof are bonded to each other by thermal welding, a hot melt adhesive, or the like to form a side seal portion 21. As a result, an underpants-type disposable diaper having a waist opening and a pair of left and right leg openings can be formed.

(Structure Example of Inner Member)

Figure 4:
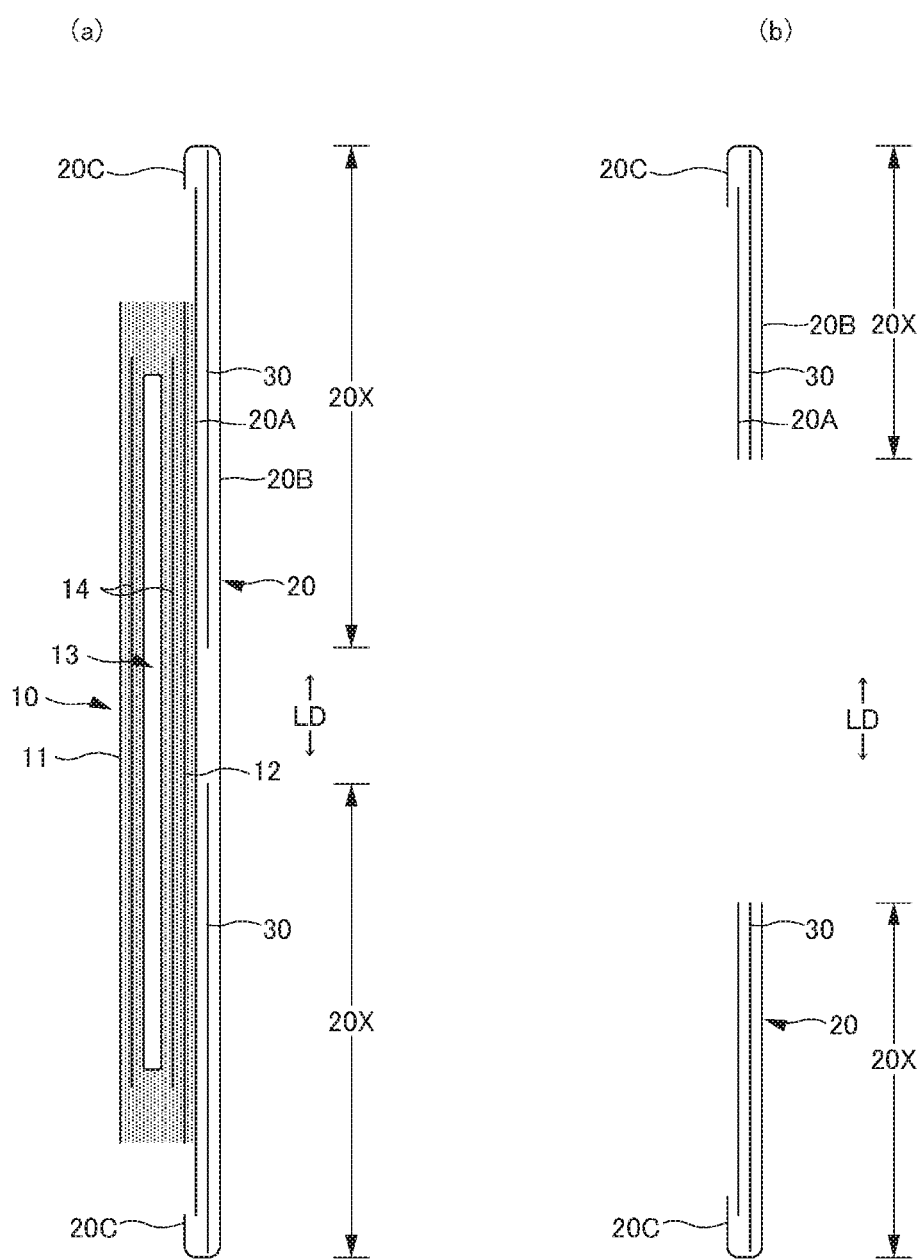
FIG. 4(a) is a cross-sectional view taken along line C-C of FIG. 1.
FIG. 4(b) is a cross-sectional view taken along line E-E of FIG. 1.
Figure 5:
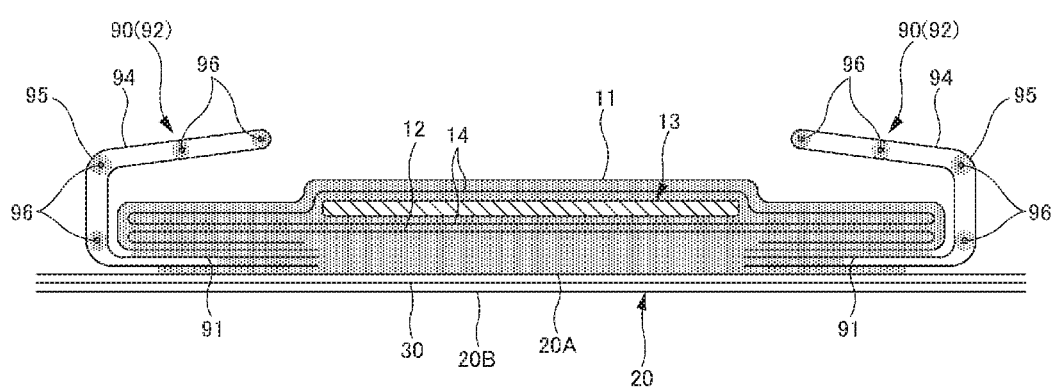
FIG. 5 is a cross-sectional view taken along line A-A of FIG. 1.
Figure 6:
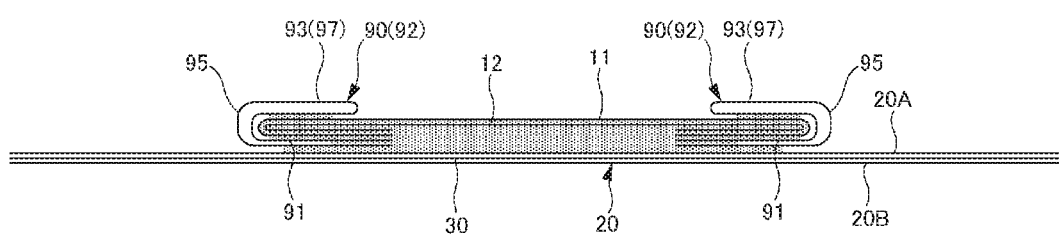
FIG. 6 is a cross-sectional view taken along line B-B of FIG. 1.

As illustrated in FIGS. 4 to 6, the inner member 10 has a structure in which the absorber 13 is interposed between the liquid pervious top sheet 11 and the liquid impervious sheet 12 made of polyethylene or the like to absorb and retain excreted fluid that has permeated through the top sheet 11. The planar shape of the inner member 10 is not particularly limited, but generally it is a substantially rectangular shape as illustrated in FIG. 1.

As the liquid pervious top sheet 11 covering a front surface side (skin side) of the absorber 13, a perforated or imperforate nonwoven fabric, a porous plastic sheet, or the like is suitably used. For a raw material fiber forming a nonwoven fabric, in addition to synthetic fibers such as polyolefin-based fibers such as polyethylene or polypropylene, polyester type, polyamide type, etc., regenerated fibers such as rayon and cupra, and natural fibers such as cotton can be used, and a nonwoven fabric obtained by an appropriate processing method, such as a spun lace method, a spun bond method, a thermal bond method, a melt blown method, and a needle punch method can be used. In these processing methods, the spun lace method is excellent in terms of flexibility and drapability, and the thermal bond method is excellent in terms of bulkiness and softness. When a large number of through holes are formed on the liquid pervious top sheet 11, urine and the like are quickly absorbed, and dry touch property is excellent. The liquid pervious top sheet 11 extends to back surface sides of the absorber 13 by wrapping up side edge portions of the absorber 13.

For the liquid impervious sheet 12 covering a back surface side (non-skin contact side) of the absorber 13, a liquid impervious plastic sheet such as polyethylene or polypropylene is used. In recent years, those having moisture permeability are preferably used from the viewpoint of prevention of stuffiness. This waterproof/moisture-pervious sheet is a microporous sheet obtained by stretching a sheet in one or two axial directions after forming the sheet by melt kneading an inorganic filler in a polyolefin resin such as polyethylene and polypropylene.

The absorber 13 is basically a known absorber, for example, accumulates of pulp fibers, assembly of filaments such as cellulose acetate, or nonwoven fabrics, and as necessary, super absorbent polymers can be mixed and fixed. The absorber 13 can be wrapped with a package sheet 14 having liquid permeability and liquid retention, such as crepe paper, as necessary, for shape and polymer retention and the like.

The absorber 13 is formed in a substantially hourglass shape having a narrowing portion 13N narrower than the front and back sides at a crotch portion. Although the size of the narrowing portion 13N can be determined as appropriate, the length in the front-back direction of the narrowing portion 13N can be set to about 20 to 50% of the entire length of the diaper, and the width of the narrowest portion is about 40 to 60% of the entire width of the absorber 13. In the case where such the narrowing portion 13N is provided, if the planar shape of the inner member 10 is substantially rectangular, a non-absorber side portion 17 without the absorber 13 is formed at a portion corresponding to the narrowing portion 13N of the absorber 13 in the inner member 10.

The liquid impervious sheet 12 is folded back to the back surface side together with the liquid pervious top sheet 11 on both sides in the width direction of the absorber 13. As this liquid impervious sheet 12, it is desirable to use an opaque sheet such that brown color of excreta, urine, and the like does not appear. As the opaque sheet, a film obtained by internally adding a pigment or a filler such as calcium carbonate, titanium oxide, zinc oxide, white carbon, clay, talc, barium sulfate, or the like in a plastic is suitably used.

Three-dimensional gathers 90 fitting around the legs are formed on both sides of the inner member 10. As illustrated in FIGS. 5 and 6, the three-dimensional gather 90 includes a fixed portion 91, a main unit section 92, a fallen portion 93, and a free portion 94. The fixed portion 91 is fixed to a side portion of a back surface of the inner member 10. The main unit section 92 extends from the fixed portion 91 through a side of the inner member 10 to above a side portion of a front surface of the inner member 10. The fallen portion 93 is formed by fixing the front and back end portions of the main unit section 92 to the side portion of the surface (the top sheet 11 in the illustrated embodiment) of the inner member 10 in a fallen state. The free portion 94 is formed by non-fixing between the fallen portions 93. Each of these portions is formed by a gather sheet 95 formed by folding a sheet such as a nonwoven fabric into a duplicate sheet. The gather sheet 95 is attached to the entire front-back direction of the inner member 10, the fallen portion 93 is provided on a front side and a back side of the non-absorber side portion 17, and the free portion 94 extends on both front and back sides of the non-absorber side portion 17. Further, between the double gather sheets 95, an elongated gather elastic member 96 is disposed at a tip portion of the free portion or the like. As illustrated in FIG. 5, in a product state, the gather elastic member 96 is for making the free portion 94 stand up by elastic contraction force.

In the form illustrated in FIGS. 5 and 6, in a portion other than the fallen non-stretchable portion 97, the gather elastic member 96 is adhered and fixed to the gather sheet 95 with a hot melt adhesive at a position of the gather elastic member 96, and opposing surfaces of the gather sheet 95 are bonded. In the fallen non-stretchable portion 97, no hot melt adhesive is provided at the position of the gather elastic member 96, and therefore, the gather elastic member 96 and the gather sheet 95 are not adhered, and an opposing surface of the gather sheet 95 is not bonded at the position having the gather elastic member 96.

The three-dimensional gather 90 illustrated in FIGS. 5 and 6 is a form in which the main unit section 92 is not folded back.

As the gather elastic member 96, materials such as polystyrene-based rubber, polyolefin-based rubber, polyurethane-based rubber, polyester-based rubber, polyurethane, polyethylene, polystyrene, styrene-butadiene copolymer, silicone, polyester, and the like which are usually used can be used. Further, in order to make it difficult to be seen from the outside, it is better that the fineness is set to 925 dtex or less, the tension is set to 150 to 350%, and the interval is set to 7.0 mm or less. As the gather elastic member 96, in addition to a thread-like shape as the illustrated embodiment, a tape-shaped member having a certain width can be used.

Like the liquid pervious top sheet 11, for a raw material fiber forming the above-described gather sheet 95, in addition to synthetic fibers such as polyolefin-based fibers such as polyethylene or polypropylene, polyester type, polyamide type, etc., regenerated fibers such as rayon and cupra, and natural fibers such as cotton can be used, and a nonwoven fabric obtained by an appropriate processing method, such as a spun bond method, a thermal bond method, a melt blown method, and a needle punch method can be used. In particular, to prevent stuffiness, nonwoven fabric having low basis weight and excellent in air permeability is preferably used. Further, with respect to the gather sheet 95, in order to prevent permeation of urine or the like and also to prevent rash and improve the feeling to the skin (dry feel), it is desirable to use a water repellent treated nonwoven fabric coated with silicone type, paraffin metal type, alkylchromic chloride type water repellent agent, etc.

As illustrated in FIGS. 3 to 6, a back surface of the inner member 10 is bonded to an inner surface of the outer member 20 with a hot melt adhesive or the like in the inner and outer fixed region 10B (shaded region). The inner and outer fixed region 10B can be determined appropriately and can be substantially the whole of the inner member 10 in the width direction WD. However, it is preferable that the both end portions in the width direction are not fixed to the outer member 20.

(Structure Example of Outer Member)

The outer member 20 extends outward from a side edge of the absorber 13. As the illustrated embodiment, in a crotch portion, the side edges of the outer member 20 may be located on the center side in the width direction form the side edges of the inner member 10 or may be located on the outer side in the width direction. Further, the outer member 20 includes a lower torso portion T which covers a range in the front-back direction corresponding to a side seal portion 21 and an intermediate portion L which covers a range in the front-back direction between the lower torso portion T of the front body F and the lower torso portion T of the back body B.

Figure 9:
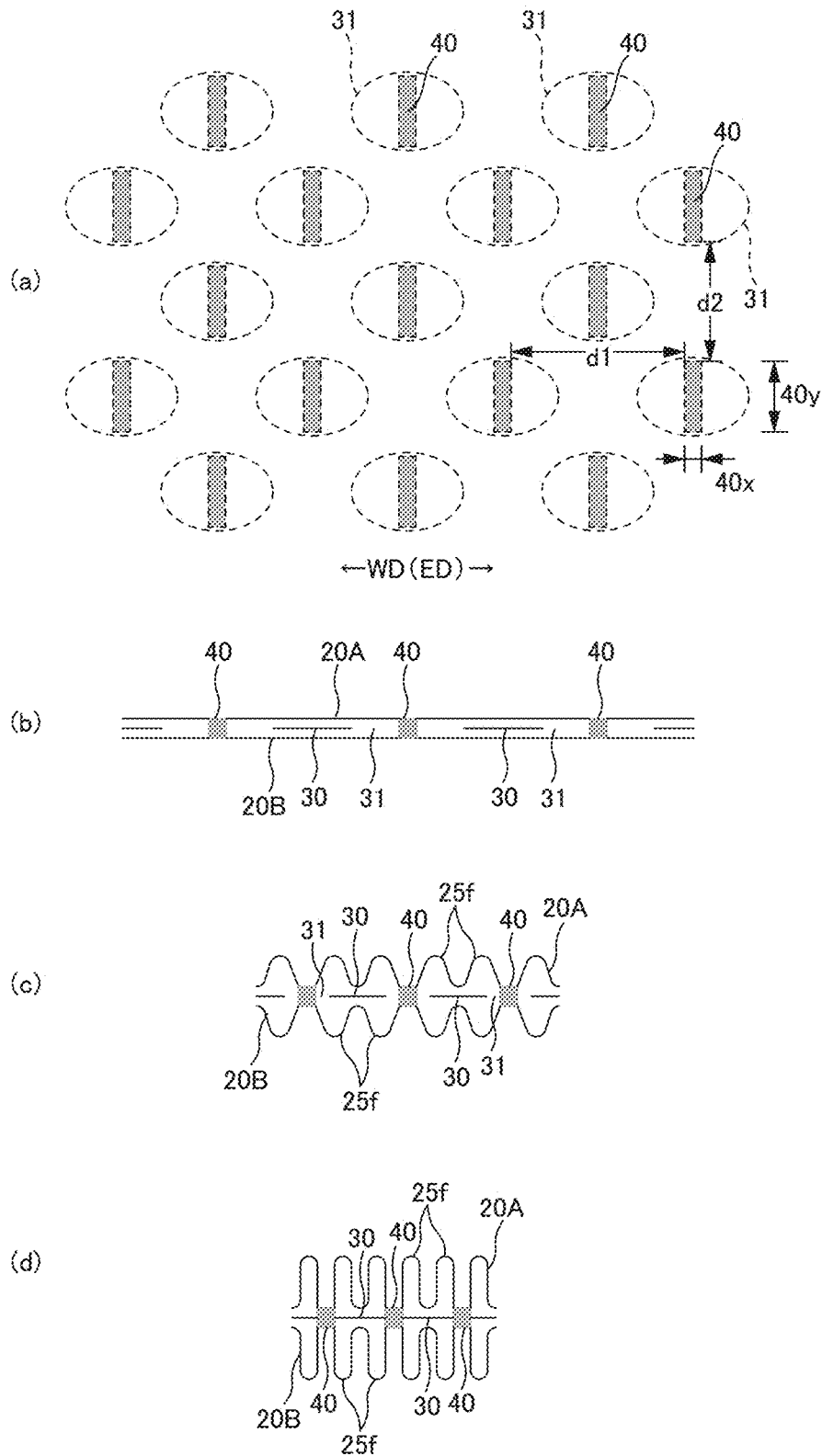
FIG. 9 is a plan view and a cross-sectional view illustrating a bonded portion arrangement disclosed in Patent Literature 1.

In the outer member 20 of the illustrated embodiment, except for the middle in the front-back direction of the intermediate portion L, as illustrated in FIGS. 2 and 4 to 6, an elastic sheet, for example, an elastic film 30, is interposed between the first sheet layer 20A and the second sheet layer 20B, and as illustrated in FIG. 9, the outer member 20 has an elastic sheet stretchable structure 20X in which the first sheet layer 20A and the second sheet layer 20B are bonded through the bonding holes 31 penetrating the elastic film 30 at a large number of sheet bonded portions 40 arranged at intervals.

In the form of application to the diaper, the stretchable direction ED of the elastic sheet (the elastic film 30 in the example of FIG. 9) is the width direction WD of the diaper.

The first sheet layer 20A and the second sheet layer 20B may be indirectly bonded via the elastic film 30, not through the bonding holes 31 of the elastic film 30. The planar shape of the outer member 20 is formed by a recessed leg around line 29 so as to form leg openings at both side edges in the width direction of the intermediate portion L and has a shape resembling an hourglass as a whole. The outer members 20 may be formed separately for the front body F and the back body B and may be arranged such that those are spaced apart in the front-back direction LD of the diaper at a crotch portion.

Figure 2:
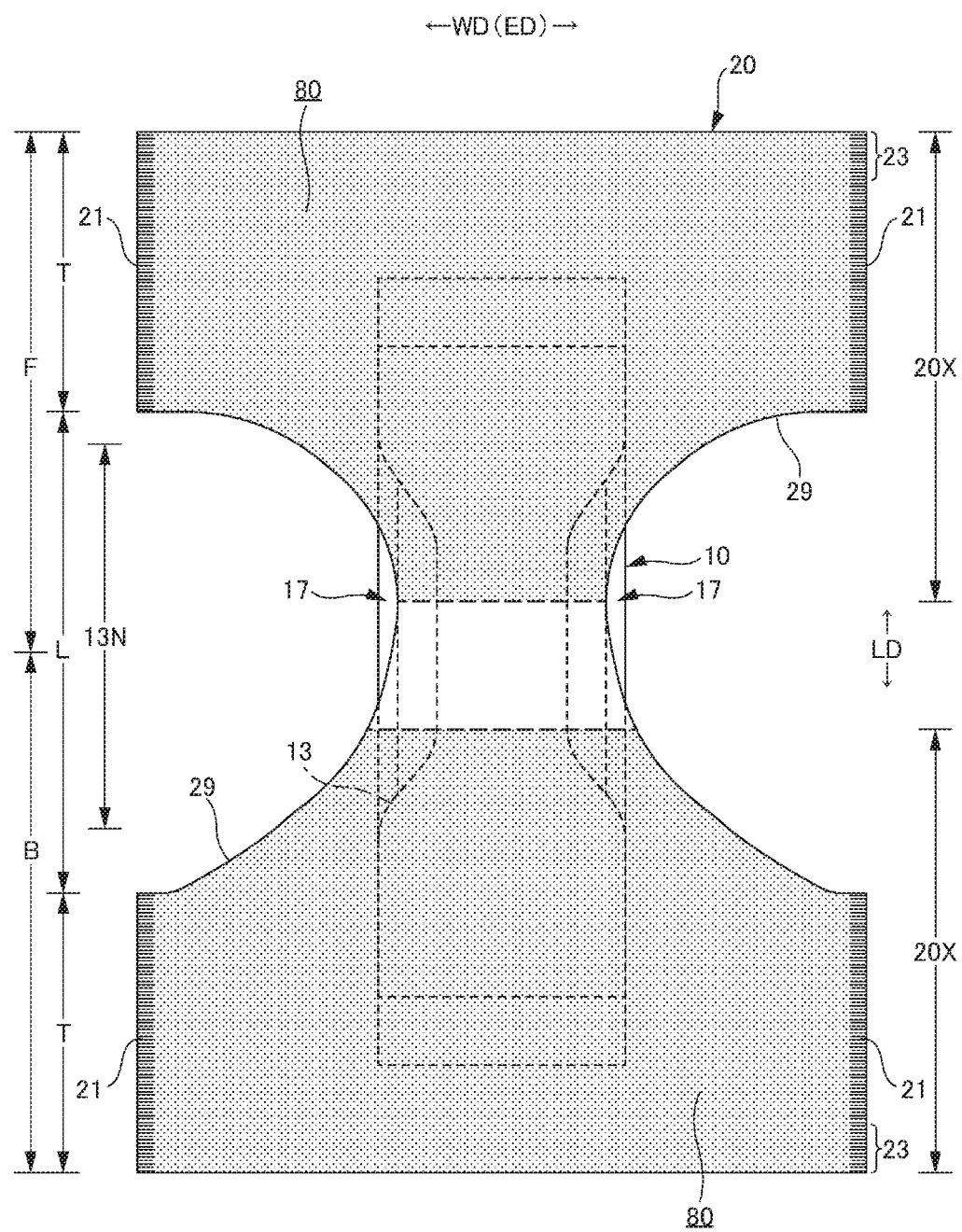
FIG. 2 is a plan view (external surface side) of an underpants-type disposable diaper in a spread state.
Figure 3:
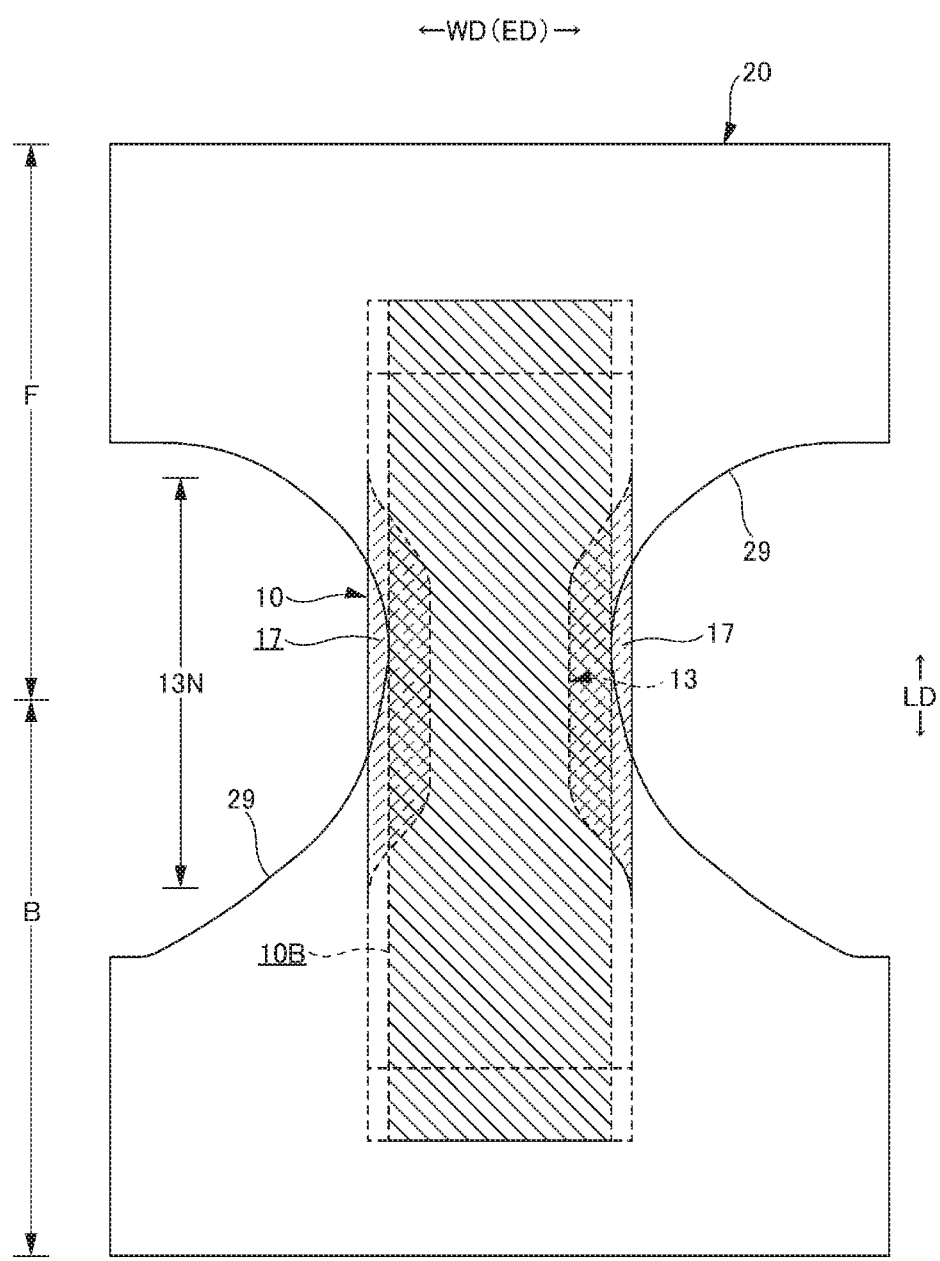
FIG. 3 is a plan view illustrating only a main part of an underpants-type disposable diaper in a spread state.

In the form illustrated in FIGS. 1 and 2, the elastic sheet stretchable structure 20X extends to a waist end portion 23. When the elastic sheet stretchable structure 20X is used in the waist end portion 23, tightening of the waist end portion 23 may be insufficient. Therefore, as illustrated FIGS. 7 and 8, without providing the elastic sheet stretchable structure 20X in the waist end portion 23, a stretchable structure by a conventional elongated waist elastic member 24 can be provided if necessary. The waist elastic member 24 is an elongated elastic member such as a plurality of rubber threads arranged at intervals in the front-back direction LD and provides a stretching force so as to tighten around the waist of a wearer. The waist elastic member 24 is not arranged substantially in a bundle with a close interval, but three or more, preferably five or more waist elastic members 24 are disposed at intervals of about 3 to 8 mm in the front-back direction so as to form a predetermined stretching zone. A stretch rate at the time of fixing the waist elastic member 24 can be appropriately determined, but it can be set to about 230 to 320% for adults usually. Although a rubber thread is used for the waist elastic member 24 in the illustrated example, another elongated elastic member such as flat rubber or the like may be used. Although not illustrated, it is also possible to provide the elastic film 30 at the waist end portion 23 and to provide the elongated waist elastic member 24 at a position overlapping with the elastic film 30 so as to have a stretchable structure by the both elastic members. Also, in the illustrated embodiment, the elongated elastic member extending along the leg opening is not provided at the edge portion of the leg opening of the outer member 20. However, an elongated elastic member may be provided at a portion overlapping with the elastic film 30 in the edge portion or in place of the elastic film 30 of the edge portion.

In another form, although not illustrated, appropriate deformation is possible such as a form that the elastic sheet stretchable structure 20X is not provided in the intermediate portion L between the lower torso portion T of the front body F and the lower torso portion T of the back body B, a form that the elastic sheet stretchable structure 20X is continuously provided in the front-back direction LD from the inside of the lower torso portion T of the front body F to the inside of the lower torso portion T of the back body B through the intermediate portion L, or a form that the elastic sheet stretchable structure 20X is provided only on one of the front body F and the back body B.

(Form of Bonded Portion)

The present invention is characterized by the arrangement of the bonded portion. In order to clarify this characteristic, the arrangement of the bonded portions in the conventional example will be specifically described.

FIG. 9 shows a representative example in Patent Literature 1.

That is, a group of the bonded portions 40 is in a staggered arrangement, the bonded portion 40 is elongated in the direction orthogonal to the stretchable direction, and has a line-symmetrical shape (left-right symmetry in FIG. 9(a)) with respect to the center line passing through the center of the stretchable direction, the width 40x of the bonded portion 40 in the stretchable direction is preferably 0.2 to 0.4 mm, the distance d1 between the bonded portions 40 arranged in the stretchable direction is 3 to 12.9 mm, more preferably 5 to 6.4 mm, and the distance d2 between the bonded portions 40 arranged in the direction orthogonal to the stretchable direction is set to 2 to 10.5 mm, more preferably 2.3 to 4.6 mm.

In this manner, the bonded portions 40 having a significantly narrow width 40x in the stretchable direction are arranged in a staggered pattern at a wide separation distance d1 in the stretchable direction to some extent, the contraction force of the elastic film 30 acts directly on each bonded portion 40. As a result of the arrangement and intervals of the bonded portions 40 being firmly maintained at the positions of the bonding holes 31 of the elastic film 30, the flexibility is less likely to deteriorate. Further, the folds 25f extend almost straight along the direction orthogonal to the stretchable direction. Moreover, the bonded portion 40 is hidden and unnoticeable between the folds 25f and the folds 25f. Therefore, the elastic sheet stretchable structure 20X having an appearance close to cloth can be obtained while suppressing a decrease in flexibility.

On the other hand, although the arrangement of the bonded portions 40 is a staggered arrangement, when the shape of the bonded portion 40 is circular, not only is the bonded portion 40 clearly visible between the folds 25f and the folds 25f of wrinkles, but also the folds 25f extends in a direction orthogonal to a stretchable direction so as to largely wrap around the bonded portion 40. Therefore, the wavy folds 25f are entirely formed, and a cloth-like appearance tends not to be obtained.

From such a viewpoint, it is desirable that the shape of the bonded portion 40 be elongated in the direction orthogonal to the stretchable direction. However, if the maximum length in the direction orthogonal to the stretchable direction of the bonded portion 40 is too short or too long, there is a possibility that the linearity of the folds 25f may be reduced, or the flexibility may be reduced. Therefore, although these dimensions can be set appropriately, the length 40y of the bonded portion 40 in the direction orthogonal to the stretchable direction is preferably 0.4 to 3.2 mm, particularly preferably 0.7 to 1.4 mm.

On the other hand, in Patent Literature 2, in both of the two examples illustrated in FIGS. 10(a) and 10(b), the arrangement of openings (illustrated by slightly elongated rectangles) of the stretchable film is also a staggered arrangement, and in the example of FIG. 10(b), the small circular sub-bonded portions are arranged between rectangular main openings. The example of FIG. 10(b) is also based on the idea of a staggered arrangement.

The arrangement and dimensions of the openings are preferably within the dimensional range (unit: mm) described in FIG. 10, mainly in terms of appearance, touch, and air permeability.

Patent Literatures 1 and 2 both disclose a vertically long opening and a staggered arrangement.

However, in the conventional example, since the separation distance between the openings of the elastic film in the direction orthogonal to the stretchable direction is set large, the stretching stress in the stretchable direction is high, and for example, some wearers might feel that they are tightened excessively (in the width direction) in the case of applying to underpants-type disposable diapers.

Here, in Patent Literature 2, although the opening length B in FIG. 10 is preferably 0.3 to 0.7 mm and the separation distance H is preferably 0.6 to 1.4 mm.

When the percentage of (separation distance between adjacent first bonded portions)/(separation distance from one point of the bonded portion to the corresponding one point of the adjacent first bonded portion) is calculated, (0.3 to 0.7 mm)/(0.6 to 1.4 mm)=21.4 to 183% is established, and although the lower limit in calculation is small, it seems that a large value is actually assumed.

On the other hand, the applicant of the present invention has found that, as illustrated in FIG. 11, when the separation distance between the openings of the elastic film in the direction orthogonal to the stretchable direction WD (ED) (an up and down direction in the drawing: direction of the reference character LD) is set small, the stretching stress in the stretchable direction can be reduced, and therefore, in the case of applying to an underpants-type disposable diaper, it is possible to gently fit to a wearer due to a weak tightening force.

The reason is thought to be that the openings are provided with a small extension force from the outside in the width direction (the stretchable direction of the elastic film), and the openings are formed in the width direction to form the bonding holes 31 as illustrated in FIG. 9, and in the separation interval region that is orthogonal to the stretchable direction between the openings, even if the region is stretched in the width direction, there are no openings, and the elongation stress of the elastic film becomes a contraction force to tighten a wearer.

The form illustrated in FIG. 11 enables gently fitting to the wearer, and also the area ratio occupied by the bonded portions and the area ratio occupied by the bonding holes in the use state of extending in the width direction are increased. Consequently there is an advantage that the air permeability is improved.

However, in the usage form in the product illustrated in FIG. 11(a), wrinkles are formed along the orthogonal direction LD in a region between a row of the bonded portions 40, 40 . . . along the orthogonal direction LD and a row of adjacent bonded portions 40, 40 . . . separated from the row in the stretchable direction WD (ED: width direction). This wrinkle 25F is simply a uniform mountain shape as illustrated in FIG. 11(b). That is, this is different from the cross section illustrated in Patent Literature 2 and shown here in FIG. 9(c).

When the form illustrated in FIG. 11 is viewed from the design perspective as the entire stretchable region of the product, a long wrinkle 25F in the orthogonal direction LD is simply and repeatedly formed in the stretchable direction ED (WD), which is a simple design, and the appeal of the product is small.

Particularly preferred embodiments will be sequentially described below with reference to typical examples.

First Embodiment

The stretchable member according to a first embodiment illustrated in FIG. 12 includes an elastic sheet stretchable structure in which an elastic sheet is interposed between a first sheet layer having air permeability and a second sheet layer having air permeability, and the first sheet layer and the second sheet layer are bonded at a plurality of sheet bonded portions arranged at intervals through bonding holes penetrating the elastic sheet or via the elastic sheet.

In addition, a stretchable region having the elastic sheet stretchable structure can expand and contract in a stretchable direction due to a contraction force of the elastic sheet.

In the present invention, the bonded portions include second bonded portions 41, 41 . . . in addition to first bonded portions 40, 40 . . . .

The first bonded portions 40, 40 . . . are arranged at intervals along the orthogonal direction LD to form a first bonded portion row.

As will be described later with reference to FIG. 19 as an eighth embodiment, for example, the rows of the first bonded portions 40, 40 . . . do not extend along the orthogonal direction LD, and the angle θ intersecting the stretchable direction ED is 30 to 150° (therefore, not including 90°), and more desirably in the range of 45 to 135° (not including 90°).

The first embodiment is an example in which the crossing angle θ that is not inclined is 90°.

The first bonded portion 40 is formed to have the orthogonal direction LD-based length L of 0.3 to 7.0 mm, preferably 0.5 to 5.0 mm, particularly preferably 0.7 to 2.5 mm.

In addition, the rows of the first bonded portions 40, 40 . . . are formed such that the formation pitch S0 based on the stretchable direction ED (WD) is 2.0 to 20.0 mm, preferably 3.0 to 15.0 mm, particularly preferably 4.0 to 10.0 mm.

Further, as the orthogonal direction LD-based distance, which is determined by the mutual relationship between the adjacent first bonded portions 40, 40 in the first bonded portions 40, 40 . . . , a percentage R of the ratio of (separation distance d between adjacent first bonded portions)/(distance P from one point of the bonded portion to a corresponding point of the adjacent first bonded portion) is 5 to 60%, preferably 10 to 45%, particularly desirably 20 to 35%.

If the percentage is excessively high, in the case of being applied to a product, a stretching stress in a width direction (stretchable direction) is high, and it tends to be difficult to obtain a suitable fit as a wearing article.

Further, if the percentage is excessively low, it is not possible to exclude the possibility that the first bonded portions 40 and 40 adjacent to the orthogonal direction LD become continuous in the manufacturing process. More fundamentally, an anvil and a heating horn that form the bonded portion are overloaded with a facility, and it may cause a hindrance to stable operation.

It is desirable that bonded portions having a length equal to or longer than the length L of the first bonded portion 40 be not formed in the rows of the second bonded portion 41 and 41. From this point of view, it is completely different from the form of FIG. 10.

In the first embodiment, the following advantages or characteristics are typically described.

(1) Since the percentage R is low, the stretching stress in the stretchable direction is low, and the stretchable sheet member has a soft elongation, and when the stretchable sheet member is applied to an absorbent article, wearing feeling is improved.

In addition, since the opening ratio increases, the air permeability increases.

(2) Since not only the rows of the first bonded portions 40, 40 . . . , but also the rows of the second bonded portions 41, 41 . . . are formed, inter-row pleats R can be formed between the rows of the first bonded portions 40, 40 . . . and the rows of the second bonded portions 41, 41 . . . .

(3) Since the second bonded portion 41 has a smaller area than the first bonded portion 40, it looks like a pattern.

(4) It is possible to form the inter-row pleats R between the first bonded portions 40, 40 . . . and the second bonded portions 41, 41. This means that it is possible to form two inter-row pleats between the rows of the first bonded portions 40, 40 . . . and the rows of the first bonded portions 40, 40 . . . . However, in the rows of the second bonded portions 41, 41 . . . , the mutual distance between the second bonded portions 41, 41 is long, and this means that the pleats can be formed without imposing an excessive burden for an anvil and a heating horn. As a result, as compared with the case where inter-row pleats are formed only by the rows of the first bonded portions 40, 40 . . . as illustrated in FIG. 11, a large number of pleats can be formed with a narrow width per unit area without burdening the equipment.

Thus, the contact area with the wearer's skin is reduced, and the comfort and the softness can be improved.

Second Embodiment

As illustrated in FIG. 13, second bonded portions 41, 41, . . . can be arranged between first bonded portions 40, 40 in an orthogonal direction LD. In this case, even if a length L of the first bonded portion 40 is short, a stretching stress can be reduced by locating the second bonded portion 41.

Third Embodiment

As illustrated in FIG. 14, second bonded portions 41 are not adjacent to first bonded portions 40 on a one-to-one basis. For example, one second bonded portion 41 is arranged adjacent to two first bonded portions 40, 40.

Fourth Embodiment

As illustrated in FIG. 15, between a row of first bonded portions 40, 40 . . . and a row of second bonded portions 41, 41 . . . , it is possible to form a row of third bonded portions 42, 42 . . . having a long separation distance in the orthogonal direction LD.

By forming the third bonded portion 42, a large pleat bf dividing the inter-row pleat R described in the first embodiment in the orthogonal direction LD can be formed.

Small pleats sf can be formed between the third bonded portion 42 and the row of the first bonded portion 40, 40 . . . .

The pleats group divided by the inter-row pleats R have low flexural rigidity of the stretchable member (easy to bend) and high followability to the movement of the body.

Fifth Embodiment

As illustrated in FIG. 16, by arranging the positions of the third bonded portions 42 obliquely together with the second bonded portions 41, a large pleat bf group having an oblique arrangement can be formed, and the design is improved.

Sixth Embodiment

As illustrated in FIG. 17, fourth bonded portions 43 can be inserted and arranged in a row of first bonded portions 40, 40 . . . . In this case, the group of the fourth bonded portions 43, 43 . . . can be arranged obliquely as illustrated in the drawing, in addition to extending in a stretchable direction ED. In this case, the area of the fourth bonded portion 43 is preferably 5% or more and 50% or less of the area of the first bonded portion 40.

Seventh Embodiment

As illustrated in FIG. 18, a first bonded portion 40 itself may be inclined. The second bonded portion 41 may also be inclined.

In the present invention, since the bonded portion length is based on the orthogonal direction LD, as illustrated in FIG. 18, the length L of the first bonded portion 40 is a length in the orthogonal direction from the center of one side to the center of the other side.

The orthogonal direction LD distance between the center of the side and the center of the opposite side is a distance d.

Eighth Embodiment

An example is shown in which, as illustrated in FIG. 19, both first bonded portions 40 and second bonded portions 41 are inclined, the row of each bonded portion is not along an orthogonal direction LD, an angle θ intersecting a stretchable direction ED is in the range of 30 to 150°, desirably 45 to 135°. The intersecting angle θ is particularly preferably 60 to 120°. However, it is obvious that 90° is not included in these angle ranges indicating the inclination.

The advantage that this bonded portion row is inclined not to extend in the orthogonal direction LD but to intersect the stretchable direction ED becomes clear by comparing with the seventh embodiment illustrated in FIG. 18. That is, in the example illustrated in FIG. 19, the reason why, for example, the separation distance between the first bonded portions 40 and 40 on the orthogonal direction LD line is considerably larger than that in the seventh embodiment illustrated in FIG. 18.

That is, for example, the bonding of the first sheet layer 20A and the second sheet layer 20B in the sheet bonded portion 40 is desirably performed by bonding means such as heat sealing or ultrasonic sealing, which is performed by welding materials.

In the case of continuous production, seal melting by ultrasonic waves is performed between anvil roll and ultrasonic horn, but, to prevent energy loss, it is important that the ultrasonic horn is in close contact with a sheet in the entire axial direction of the anvil roll. For this reason, it is necessary to output a large ultrasonic wave to form a pattern with a large proportion of anvil roll convex portions, such as the rows of the bonded portions 40, 40 . . . in FIG. 12 along the bus that makes line contact. Therefore, if an excessive close force is applied along a bus that makes line contact, a facility load is increased.

On the contrary, in the case of the eighth embodiment illustrated in FIG. 19 (generally in the case of an inclined arrangement), the proportion of the bonded portions located on the line in the orthogonal direction LD is small, and the line pressure is stable, such that the facility load is decreased, and stable operation is possible.

In the eighth embodiment illustrated in FIG. 19, since the first bonded portion 40 (and the second bonded portion 41) is inclined, there is also an advantage that folds and pleats excellent in design can be formed.

Ninth Embodiment

In a ninth embodiment illustrated in FIG. 20, a rows of first bonded portions 40, 40 . . . and a rows of second bonded portions 41, 41 . . . follow a waveform curve swinging in a stretchable direction ED.

The arrangement of the waveform curves is excellent in appearance.

Tenth Embodiment

A tenth embodiment illustrated in FIG. 21 is such that large pleats bf follow a waveform curve swinging in an orthogonal direction LD. The arrangement of the waveform curves is also excellent in appearance.

Eleventh Embodiment

According to an eleventh embodiment illustrated in FIG. 22, first bonded portions 40, 40 . . . and second bonded portions 41, 41 . . . follow the waveform curve swinging in a stretchable direction ED, and inclining large pleats bf follow a waveform curve swinging in an orthogonal direction LD. The arrangement of the waveform curves enables formation of complicated pleats, and is excellent in appearance.

Further, embodiments of the present invention will be described.

The shape of each of sheet bonded portions 40 and bonding holes 31 in a natural length state can be appropriately determined, in addition to a rectangle described above. For example, as illustrated in FIG. 23, the shape can be an arbitrary shape such as a perfect circle, a triangle, a polygon, a star, a cloud, and the like in addition to a convex lens shape (refer to FIG. 23(a)), a diamond shape (refer to FIG. 23(b)), a concave lens shape (refer to FIG. 23 (c)), and an elliptical shape (refer to FIG. 23(d)).

The bonding hole 31 mainly relates to the shape of the bonded portion 40 (41, 42, 43), the manufacturing stage, or the stretchable degree.

In the case where the first sheet layer 20A and the second sheet layer 20B in the sheet bonded portion 40 is bonded through the bonding hole 31 formed on the elastic film 30, it is desirable that the first sheet layer 20A and the second sheet layer 20B be not bonded to the elastic film 30 at least in a portion other than between the first sheet layer 20A and the second sheet layer 20B in the sheet bonded portion 40.

Means for bonding the first sheet layer 20A and the second sheet layer 20B in the sheet bonded portion 40 is not particularly limited. For example, in the sheet bonded portion 40, the first sheet layer 20A and the second sheet layer 20B may be bonded with a hot melt adhesive or may be bonded by means of material welding such as heat sealing or ultrasonic sealing.

In the case where the first sheet layer 20A and the second sheet layer 20B are bonded through the bonding hole 31 of the elastic film 30 in the sheet bonded portion 40, as a form in which the sheet bonded portion 40 is formed by material welding, a first welding form, a second welding form, and a third welding form may be used. In the first welding form, the first sheet layer 20A and the second sheet layer 20B are bonded only by melt-solidified material 20m of the most of or a part of at least one of the first sheet layer 20A and the second sheet layer 20B in the sheet bonded portion 40 (refer to FIG. 24(a)). In the second welding form, the first sheet layer 20A and the second sheet layer 20B are bonded only by the melt-solidified material 30m of the whole of, the most of, or a part of the elastic film 30 in the sheet bonded portion 40 (refer to FIG. 24(b)). In the third welding form, the first welding form and the second welding form are combined (refer to FIG. 24(c)). However, the second welding form and the third welding form are preferable.

In particular, a form is preferable in which the first sheet layer 20A and the second sheet layer 20B are bonded by the melt-solidified material 20m of a part of the first sheet layer 20A and the second sheet layer 20B and the melt-solidified material 30m of the whole of or the most of the elastic film 30 in the sheet bonded portion 40. In the third welding form illustrated in FIG. 26(b), the melt-solidified material 30m of the elastic film 30 shown in white is found between the melt-solidified materials 20m of fibers of the first sheet layer 20A or the second sheet layer 20B shown in black. However, in the first welding form illustrated in FIG. 26(a), the melt-solidified material of the elastic film is not seen between the melt-solidified materials 20m of fibers of the first sheet layer 20A or the second sheet layer 20B.

Like the first bonding form and the third bonding form, when the first sheet layer 20A and the second sheet layer 20B are bonded by the melt-solidified material 20m of the most of or a part of at least one of the first sheet layer 20A and the second sheet layer 20B as an adhesive, it is preferable that a part of the first sheet layer 20A and the second sheet layer 20B are not melted since the sheet bonded portion 40 does not harden.

When the first sheet layer 20A and the second sheet layer 20B are nonwoven fabrics, a case in which a part of the first sheet layer 20A and the second sheet layer 20B do not melt, includes a form in which although the core (including not only the core of a composite fiber but also the central portion of a single component fiber) remains for all the fibers of the sheet bonded portion 40, the peripheral portion (including not only a sheath in a conjugate fiber but also a surface layer side portion of a single component fiber) is melted, and a form in which a part of the fibers do not melt at all, but the remaining fibers melt all, or the core remains but the surrounding portion melts.

When the first sheet layer 20A and the second sheet layer 20B are bonded using the melt-solidified material 30m of the elastic film 30 as an adhesive like the second welding form and the third welding form, the peel strength becomes high. In the second welding form, under the condition that a melting point of at least one of the first sheet layer 20A and the second sheet layer 20B is higher than the melting point of the elastic film 30 and a heating temperature at the time of forming the sheet bonded portion 40, the elastic film 30 is sandwiched between the first sheet layer 20A and the second sheet layer 20B, and a portion to be the sheet bonded portion 40 is pressurized and heated such that only the elastic film 30 is melted at the time of manufacture.

On the other hand, in the third welding form, under the condition that a melting point of at least one of the first sheet layer 20A and the second sheet layer 20B is higher than a melting point of the elastic film 30, the elastic film 30 is sandwiched between the first sheet layer 20A and the second sheet layer 20B, and a portion to be the sheet bonded portion 40 is pressurized and heated such that at least one of the first sheet layer 20A and the second sheet layer 20B and the elastic film 30 are melted at the time of manufacture.

From such a viewpoint, the melting point of the elastic film 30 is preferably about 80 to 145° C., and the melting point of the first sheet layer 20A and the second sheet layer 20B is preferably about 85 to 190° C., particularly preferably 150 to 190° C. The difference between the melting points of the first sheet layer 20A and the second sheet layer 20B and the melting point of the elastic film 30 is preferably about 60 to 90° C. The heating temperature is preferably about 100 to 150° C.

In the second welding mode and the third welding mode, when the first sheet layer 20A and the second sheet layer 20B are nonwoven fabrics, the melt-solidified material 30m of the elastic film 30 may penetrate into fibers in the entire thickness direction of the first sheet layer 20A and the second sheet layer 20B in the sheet bonded portion 40 as illustrated in FIG. 25(c). However, as illustrated in FIG. 25(a), in the form in which the melt-solidified material 30m penetrates into fibers to the middle of the thickness direction or in the form in which the melt-solidified material 30m does not almost penetrate into the fibers of the first sheet layer 20A and the second sheet layer 20B as illustrated in FIG. 25(b), the flexibility of the sheet bonded portion 40 is further improved.

FIG. 27 shows an example of an ultrasonic sealing device suitable for forming the second welding form and the third welding form. This ultrasonic sealing device feeds the first sheet layer 20A, the elastic film 30, and the second sheet layer 20B between an anvil roll 60 having a protruding portion 60a formed in a pattern of the sheet bonded portion 40 on the outer surface and an ultrasonic horn 61 for forming the sheet bonded portion 40. At this time, for example, by setting a feed moving speed of the elastic film 30 by a feed drive roll 63 and a nip roll 62 on the upstream side to be slower than a conveying speed on the downstream of the anvil roll 60 and the ultrasonic horn 61, the elastic film 30 is elongated in the MD direction (machine direction, flow direction) at a predetermined stretch rate in a path from a nip position by the feed drive roll 63 and the nip roll 62 to a sealing position by the anvil roll 60 and the ultrasonic horn 61. The stretch rate of the elastic film 30 can be set by selecting a speed difference between the anvil roll 60 and the feed drive roll 63 and can be set to, for example, about 300% to 500%. The reference sign 62 denotes a nip roll.

The first sheet layer 20A, the elastic film 30, and the second sheet layer 20B, which are fed between the anvil roll 60 and the ultrasonic horn 61, are laminated in this order, and while pressurizing between the protruding portion 60a and the ultrasonic horn 61, those are heated by ultrasonic vibration energy of the ultrasonic horn 61. The bonding hole 31 is formed in the elastic film 30 by melting only the elastic film 30 or melting at least one of the first sheet layer 20A and the second sheet layer 20B and the elastic film 30, and simultaneously the first sheet layer 20A and the second sheet layer 20B are bonded through the bonding hole 31. Therefore, in this case, by selecting the size, shape, separation distance, arrangement pattern in the roll length direction and roll circumferential direction, etc. of the protruding portion 60a of the anvil roll 60, the area ratio of the sheet bonded portion 40 can be selected.

The reason why the bonding hole 31 is formed is not necessarily clear, but it is considered that a portion corresponding to the protruding portion 60a of the anvil roll 60 in the elastic film 30 melts, and a hole opens by detaching from the surroundings. At this time, as illustrated in FIGS. 9(*a*) and 11(*a*), the portion of the elastic film 30 between the adjacent bonding holes 31 aligned in the stretchable direction ED is cut from the portion of both sides in the stretchable direction by the through hole 31 and loses support on both sides in a contraction direction. Therefore, the portion shrinks in a range, in which the continuity in the direction orthogonal to the contraction direction is secured, until the center side of the direction LD orthogonal to the stretchable direction ED balances with the center side of the stretchable direction, and the bonding hole 31 expands in the stretchable direction ED.

The constituent materials of the first sheet layer 20A and the second sheet layer 20B are not particularly limited as long as they are in the form of a sheet, but it is preferable to use a nonwoven fabric from the viewpoints of air permeability and flexibility. In the nonwoven fabric, a raw material fiber thereof is not particularly limited. Examples of the nonwoven fabric can include synthetic fibers such as polyolefin-based fibers such as polyethylene and polypropylene, polyester type, and polyamide type, regenerated fibers such as rayon and cupra, natural fibers such as cotton, mixed fibers and composite fibers in which two or more of these are used. Further, the nonwoven fabric may be manufactured by any processing.

Examples of the processing method include known methods such as a spun lace method, a spun bond method, a thermal bond method, a meltblown method, a needle punch method, an air-through method, and a point bond method.

When a nonwoven fabric is used, its basis weight is preferably about 10 to 25 g/m$^2$. Further, a part or the whole of the first sheet layer 20A and the second sheet layer 20B may be a pair of layers in which a single material is folded back to face each other. For example, as in the illustrated embodiment, in the waist end portion 23, the constituent material located on the outer side is regarded as the second sheet layer 20B, and the folded portion 20C folded back to the inner surface side at a waist opening edge is regarded as the first sheet layer 20A, and an elastic film 30 is interposed therebetween. In the other portions, the constituent material located on the inner side is regarded as the first sheet layer 20A, the constituent material located on the outer side is regarded as the second sheet layer 20B, and the elastic film 30 can be interposed therebetween. It is obvious that the constituent material of the first sheet layer 20A and the constituent material of the second sheet layer 20B can be individually provided over the entire front-back direction LD, and without folding back the constituent materials, the elastic film 30 may be interposed between the constituent material of the first sheet layer 20A and the constituent material of the second sheet layer 20B.

The elastic film 30 is not particularly limited, and any elastic thermoplastic resin film which has elasticity such as an imperforate one and those having many holes and slits for ventilation can also be used. In particular, in the elastic film 30, the tensile strength in the width direction WD (stretchable direction ED, MD direction) is preferably 8 to 25 N/35 mm, the tensile strength in the front-back direction LD (direction LD orthogonal to the stretchable direction, CD direction) is preferably 5 to 20 N/35 mm, the tensile elongation in the width direction WD is preferably 450 to 1050%, and the tensile elongation in the front-back direction LD is preferably 450 to 1400%. The thickness of the elastic film 30 is not particularly limited, but it is preferably about 20 to 40 μm.

(Stretchable Region)

A region having the elastic sheet stretchable structure 20X in the outer member 20 has a stretchable region that can expand and contract in the width direction WD. In the stretchable region 80, the elastic film 30 has a portion 32 linearly continuing along the width direction WD (refer to FIG. 12(*a*)), and the elastic film 30 contracts in the width direction WD due to a contraction force of the elastic film 30 and can be stretched in the width direction WD. More specifically, with the elastic film 30 extended in the width direction WD, the first sheet layer 20A and the second sheet layer 20B are bonded via the bonding hole 31 of the elastic film 30 with a space in the width direction WD and the front-back direction LD (direction LD orthogonal to the stretchable direction) orthogonal to the width direction WD to form a large number of sheet bonded portions 40, thus forming the elastic sheet stretchable structure 20X. In addition, by arranging the bonding holes 31 such that the elastic film 30 has a linearly continuous portion 32 along the width direction WD (refer to FIG. 12(*a*)) in the stretchable region 80, such elasticity can be imparted.

In a natural length state, as illustrated in FIGS. 9 and 12(*b*) in the stretchable region, the first sheet layer 20A and the second sheet layer 20B between the sheet bonded portions 40 bulge in directions away from each other, shrinkage wrinkles 25*f* and 25F extending in the front-back direction LD are formed, and the shrinkage wrinkles 25F are stretched even in a wearing state extended to some extent in the width direction WD, but those remain. In addition, as the illustrated embodiment, when the first sheet layer 20A and the second sheet layer 20B are not bonded to the elastic film 30 at least at a space other than between the first sheet layer 20A and the second sheet layer 20B in the sheet bonded portion 40, as can be seen from the FIG. 9(c) assuming the mounting state and FIG. 9(a) assuming a spread state of the first sheet layer 20A and the second sheet layer 20B, in these states, a gap is formed between bonding holes 31 in the elastic film 30 and the sheet bonded portions 40, and even if a material of the elastic film 30 is a non-porous film and sheet, air permeability is imparted by this gap. In addition, in the natural length state, the bonding hole 31 is narrowed by further contraction of the elastic film 30, and a gap is not formed almost between the bonding hole 31 and the sheet bonded portion 40.

It is desirable that the elastic limit elongation of the stretchable region 80 in the width direction WD be 200% or more (preferably 265 to 295%). The elastic limit elongation of the stretchable region 80 is substantially determined by the stretch rate of the elastic film 30 at the time of manufacture. On the basis of this, the elastic limit elongation rate decreases due to a factor of inhibiting shrinkage in the width direction WD. The main cause of such inhibition is a ratio of the length L of the sheet bonded portion 40 to a unit length in the width direction WD, and the elastic limit elongation decreases as this ratio increases. In the usual case, since the length L of the sheet bonded portion 40 is correlated with the area ratio of the sheet bonded portion 40, the elastic limit elongation of the stretchable region 80 can be adjusted by the area ratio of the sheet bonded portion 40.

The elongation stress of the stretchable region 80 can be adjusted mainly by a sum of the orthogonal direction LD distances (separation distance d) of the portions 32 (refer to FIG. 12(a)) where the elastic film 30 is linearly continuous along the width direction WD.

The area ratio of the sheet bonded portion 40 and the area of the individual sheet bonded portion 40 in the stretchable region 80 can be appropriately determined, but in the usual case, it is preferable to be within the following range.

The area of the seat bonded portion 40: 0.14 to 3.5 mm$^2$ (particularly 0.14 to 1.0 mm$^2$)

The area ratio of the sheet bonded portion 40: 1.8 to 19.1% (particularly 1.8 to 10.6%)

Figure 7:
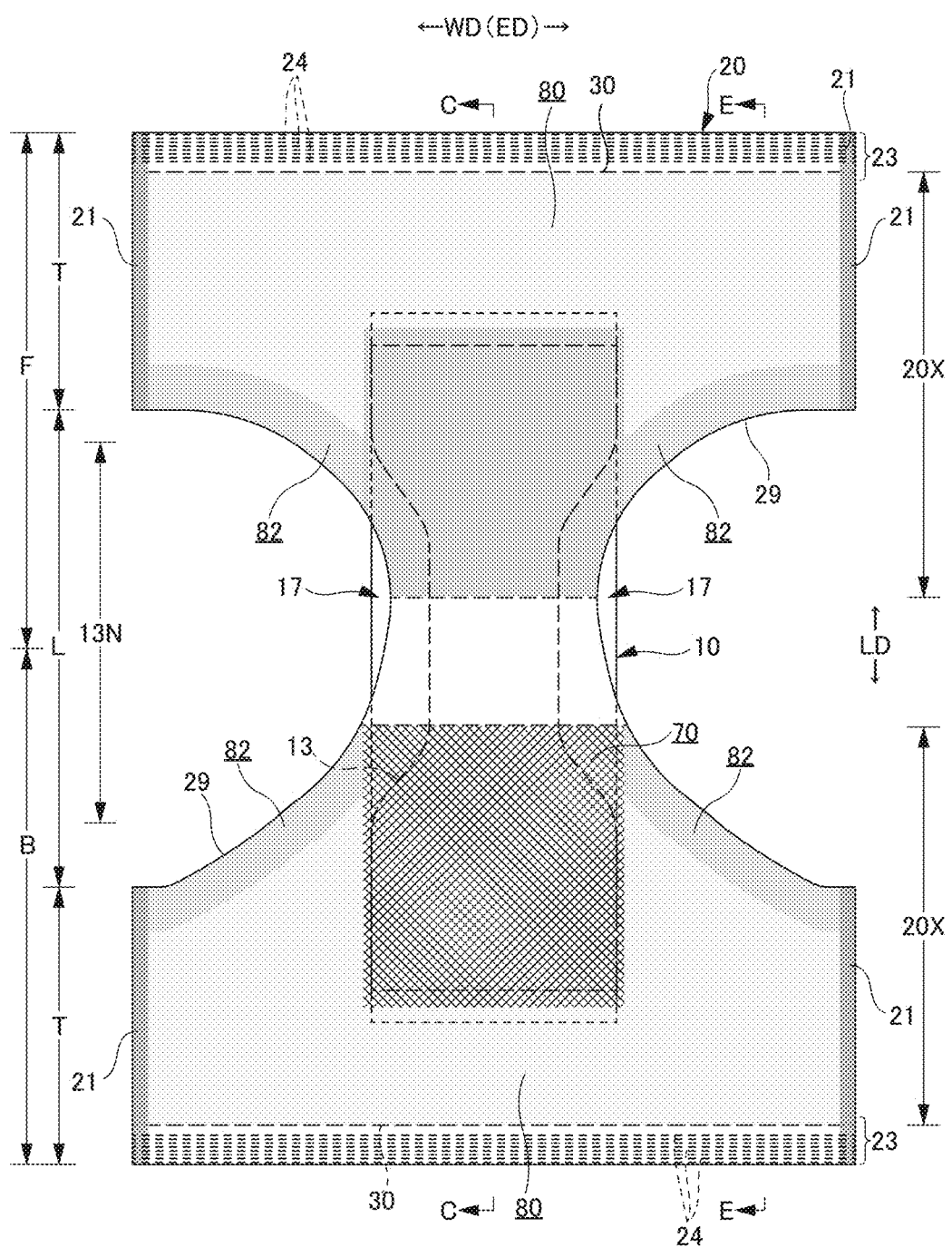
FIG. 7 is a plan view (internal surface side) of a main part of a stretchable region of an underpants-type disposable diaper in a spread state.
Figure 8:
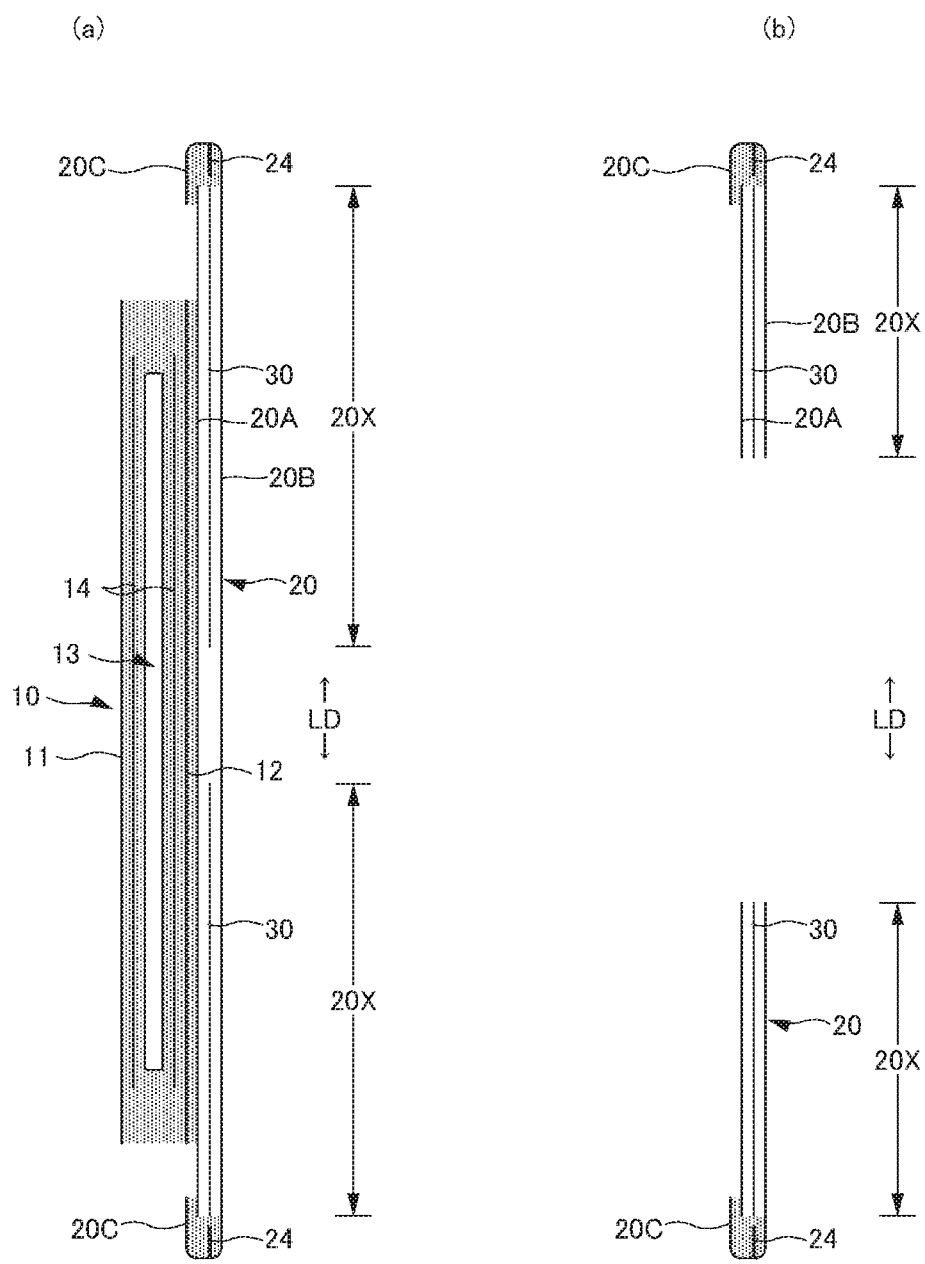
FIG. 8(a) is a cross-sectional view corresponding to line C-C of FIG. 1.
FIG. 8(b) is a cross-sectional view corresponding to line E-E of FIG. 1.

In this way, since the elastic limit elongation and elongation stress of the stretchable region 80 can be adjusted by the area of the sheet bonded portion 40, as illustrated in FIG. 7, a plurality of regions having different area ratios of the sheet bonded portion 40 in the stretchable region 80 is provided to change the fitting according to a site. In the form illustrated in FIG. 7, an edge stretchable region 82 of a leg opening is provided, the edge stretchable region 82 is a region in which the area ratio of sheet bonded portions 40 is higher than that of the other regions, and therefore the elongation stress is weak, and the region flexibly expands and contracts.

(Non-Stretchable Region)

As illustrated in FIG. 7, the non-stretchable region 70 can be provided on at least one side in the width direction of the stretchable region 80 in the region of the outer member 20 having the elastic sheet stretchable structure 20X. The arrangement of the stretchable region 80 and the non-stretchable region 70 can be appropriately determined. In the case of the outer member 20 of the underpants-type disposable diaper according to the present embodiment, since the part overlapping with the absorber 13 is a region unnecessary to expand and contract, as the illustrated embodiment, a part or all of the portion overlapping with the absorber 13 (it is desirable to include nearly the entire inner and outer fixing regions 10B) is preferably the non-stretchable region 70. It is obvious that the non-stretchable region 70 can be provided from a region overlapping with the absorber 13 to a region not overlapping with the absorber 13 located in the width direction WD or the front-back direction LD, and the non-stretchable region 70 can be provided only in the region not overlapping with the absorber 13.

In the non-stretchable region 70, although the elastic film 30 continues in the width direction WD, the elastic film 30 does not have a linearly continuous portion along the width direction WD due to the presence of the bonding hole 31. Therefore, with the elastic film 30 extended in the width direction WD, the first sheet layer 20A and the second sheet layer 20B are bonded to each other through the bonding hole 31 of the elastic film 30 with a space therebetween in the width direction WD and the front-back direction LD orthogonal thereto to form a large number of the sheet bonded portions 40. As a result, even if the whole of the elastic sheet stretchable structure 20X including both the stretchable region 80 and the non-stretchable region 70 is formed, the elastic film 30 does not linearly continue along the width direction WD in the non-stretchable region 70, such that a contraction force of the elastic film 30 hardly acts on the first sheet layer 20A and the second sheet layer 20B, and elasticity almost disappears, and elastic limit elongation approaches 100%.

In such non-stretchable region 70, the first sheet layer 20A and the second sheet layer 20B are bonded at a large number of sheet bonded portions 40 arranged with a space therebetween, and the sheet bonded portion 40 is not continuous. Therefore, a decrease in flexibility is prevented.

The arrangement pattern of the bonding holes 31 in the elastic film 30 in the non-stretchable region 70 can be appropriately determined.

The area ratio of the sheet bonded portion 40 and the area of the individual sheet bonded portion 40 in the non-stretchable region can be appropriately determined, but in the usual case, it is preferable that the area is within the following range, since the non-stretchable region 70 is not hardened due to the small area of each sheet bonded portion 40 and the low area ratio of each sheet bonded portion 40.

The area of the sheet bonded portion 40: 0.10 to 0.75 mm$^2$ (particularly 0.10 to 0.35 mm$^2$)

The area ratio of the sheet bonded portion 40: 4 to 13% (particularly 5 to 10%)

In the above example, an elastic film is used as the elastic sheet. However, elastic nonwovens can also be used. Further, an elastic nonwoven fabric is provided on one side or both sides of the elastic film, and this can be interposed between the first sheet layer 20A and the second sheet layer 20B.

Explanation of Terms Used Herein

The following terms in the specification have the following meanings unless otherwise specified in the specification.

"Front body" and "back body" mean front and back portions, respectively, with the center in the front-back direction of an underpants-type disposable diaper as a boundary. In addition, a crotch portion means a front-back direction range including the center in the front-back direction of an underpants-type disposable diaper, and in the case where an absorber has a narrowing portion, it means a range in the front-back direction of the portion having the narrowing portion.

"Elastic limit elongation" means the elongation of the elastic limit in the stretchable direction ED (in other words, the state in which the first sheet layer and the second sheet layer are completely developed), and the length at the elastic limit is expressed as a percentage in the case where a natural length is assumed to be 100%.

"Area ratio" means a ratio of a target portion to a unit area. The area ratio is expressed as a percentage by dividing a total area of the target portion (for example, the sheet bonded portion 40, an opening of the bonding hole 31, a vent hole) in the target region (for example, the stretchable region 80, and the non-stretchable region 70) by the area of the target region. In particular, the "area ratio" in the region having the stretchable structure means an area ratio in a state where it is extended to the elastic limit in the stretchable direction ED. In a form in which a large number of target portions are provided at intervals, it is desirable to set the target region to a size such that ten or more target portions are included and obtain the area ratio.

"Stretch rate" means the value when the natural length is taken as 100%.

"Basis weight" is measured as follows. After preliminary drying a sample or a test piece, the sample or the test piece is left in a test chamber or equipment in the standard state (the test location is at a temperature of 23±1° C. and with a relative humidity of 50±2%) to be constant weight. The preliminary drying refers to making a sample or a test piece a constant weight in an environment at a temperature of 100° C. For fibers with an official moisture regain of 0.0%, preliminary drying may not be performed. A sample of dimensions of 100 mm×100 mm is cut using a template for sampling (100 mm×100 mm) from a test piece in a constant weight. The basis weight is set by weighing the sample, multiplying by 100, and calculating the weight per one square meter.

"Thickness" of an absorber is measured using a thickness measuring instrument (Peacock, large dial gauge type, model J-B (measurement range 0 to 35 mm) or model K-4 (measurement range 0 to 50 mm)) manufactured by Ozaki Seisakusho Co., Ltd., and a sample and the thickness measuring instrument are set to be horizontal.

"Thickness" other than the above is automatically measured under the conditions of a load of 0.098 N/cm$^2$ and a pressing area of 2 cm$^2$ using an automatic thickness measuring device (KES-G5 handy compression measuring program).

"Tensile strength" and "tensile elongation (breaking elongation)" mean values obtained by measuring with an initial chuck distance (gauge length) of 50 mm and a tensile speed of 300 mm/min according to JIS K7127: 1999 "Test method of plastic-tensile properties-" except that the test piece is formed into a rectangular shape having a width of 35 mm×a length of 80 mm. As a tensile testing machine, for example, AUTOGRAPH AGS-G100N manufactured by SHIMADZU corporation can be used.

"Elongation stress" means a tensile stress (N/35 mm) measured when extending in the stretchable region by a tensile test in which the initial chuck distance (gauge length) is 50 mm, and the tensile speed is 300 mm/min according to JIS K7127: 1999 "Test method of plastic-tensile properties—", and the degree of elongation can be appropriately determined depending on the test target. It is preferable that the test piece has a rectangular shape with a width of 35 mm and a length of 80 mm or more, but when a test piece with a width of 35 mm cannot be cut out, a test piece is formed with a width that can be cut out, and the measured value is obtained based on 35 mm in width. Even if the target area is small, and it is not possible to collect a sufficient test piece, as long as comparing the magnitude of the elongation stress, a small test specimen can be also compared at least as long as a test piece of the same size is used. As a tensile testing machine, for example, AUTOGRAPH AGS-G100N manufactured by SHIMADZU corporation can be used.

"Spread state" means a flatly spread state without shrinkage or slackness.

The dimension of each part means the dimension in the spread state, not the natural length state, unless otherwise stated. In particular, the size of the bonded portion is a size in a state of being developed to the limit (state before the first sheet layer and the second sheet layer are broken), and substantially matches the size of the bonded portion pattern in the anvil roll.

When environmental conditions in tests and measurements are not described, the tests and measurements shall be carried out in a test room or apparatus in a standard state (a temperature of 23±1° C. and a relative humidity of 50±2% at the test location).

On the other hand, as described above, an object of the present invention is to prevent or suppress the occurrence of tearing of an elastic film between stretchable regions in an elastic sheet stretchable structure.

For example, in the case where the Z range between the stretchable region 80 on the side portion of the diaper illustrated in FIG. 7 and the edge stretchable region 82 of the leg opening is separated as illustrated in FIG. 28, when the diaper is stretched in the width direction for wearing, a tear Q of the elastic film may occur, which is considered to be caused by the difference in thermal damage in the separation of the stretchable regions having different arrangement patterns.

On the other hand, according to the present invention, for example, as illustrated in FIG. 29, at the boundary between the first stretchable region E1 and the second stretchable region E2, in which at least one of the arrangement pattern of the bonded portion and the shape of the bonded portion is different, by setting the separation distance Px between a bonded portion located on the side of the boundary of the first stretchable region E1 in the stretchable direction ED and a bonded portion located on the side of the boundary of the second stretchable region E2 in the stretchable direction ED in the elastic limit elongation state to 10 mm or less, the occurrence of tearing of the elastic film can be prevented or suppressed.

In this case, the separation distance Px in the stretchable direction ED (width direction WD in a diaper) is more preferably 7 mm or less, and particularly preferably 5 mm or less. Although there is no limit on the lower limit, a lowering of Px means that the above-described S0 becomes small as the arrangement pattern of the bonded portion, such that the lower limit of the separation distance Px is desirably 2 mm.

The separation distance Py in the orthogonal direction LD (the front-back direction in a diaper) orthogonal to the stretchable direction ED is 10 mm or less, desirably 7 mm or less, and particularly preferably 5 mm or less. It is desirable that the lower limit be 2 mm.

The separation distance Py in the orthogonal direction LD has little correlation with tearing of the elastic film. However, particularly when the angle θ intersecting the stretchable direction ED is small, the above range is desirable since the correlation with the tearing of the elastic film becomes large.

The arrangement pattern of the first stretchable region E1 in FIG. 29 is similar to the arrangement pattern of FIG. 12, and the second bonded portions 41 correspond to the first bonded portions 40 one to one. In the arrangement pattern of the second stretchable region E2, the horizontally long first bonded portions 40A are arranged.

There is no limitation on the arrangement pattern of the first stretchable region E1 and the second stretchable region E2. In the example of FIG. 30, the first stretchable region E1 is the same as the arrangement pattern of FIG. 15 in which the third bonded portion 42 is formed.

The rows of the bonded portions of the first stretchable region E1 and the second stretchable region E2 are aligned with the stretchable direction ED and the orthogonal direction LD as illustrated in FIG. 31, and also the rows may be inclined at the angle θ that intersects the stretchable direction ED as illustrated in FIGS. 19, 29, 30, and 32.

FIG. 31 indicates the positions of the separation distance Px and the separation distance Py when the rows of the bonded portions of the first stretchable region E1 and the second stretchable region E2 are aligned in the stretchable direction ED and the orthogonal direction LD.

On the other hand, by providing the intermediate region E3 between the first stretchable region E1 and the second stretchable region E2, it is possible to prevent or suppress the occurrence of tearing of the elastic film.

Figure 32:
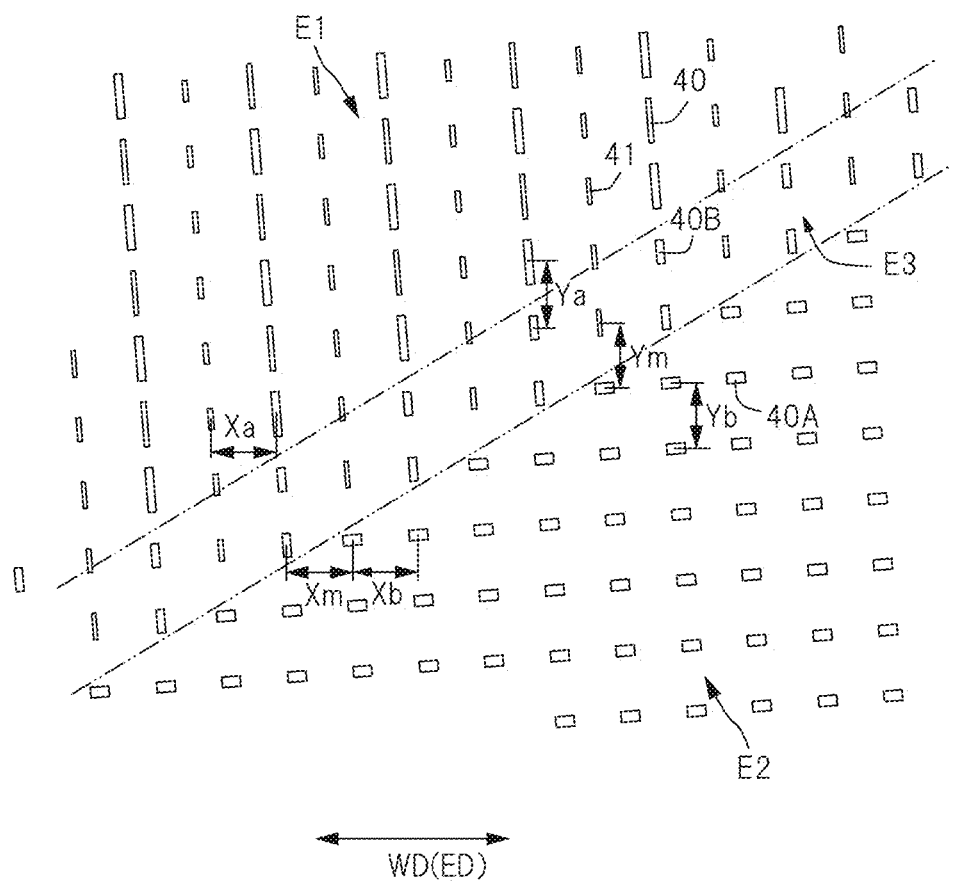
FIG. 32 is a plan view of a fourth example of a stretchable region according to the present invention.

For example, the example of FIG. 32 shows, as the intermediate region E3, an arrangement pattern in which first bonded portions 40B having a short length in comparison with the arrangement pattern of the bonded portions of FIG. 29 is formed.

In this case, at the boundary between the first stretchable region E1 and the intermediate region E3, the separation distance Px is 10 mm or less. Further, at the boundary between the intermediate region E3 and the second stretchable region E2, the separation distance Px is preferably 10 mm or less.

Further, in the case where
(1) a pitch of the bonded portions in the intermediate stretchable region in a stretchable direction is Xm,
(2) a pitch of the bonded portions in the first stretchable region in a stretchable direction is Xa, and
(3) a pitch of the bonded portions in the second stretchable region in a stretchable direction is Xb,
it is desirable that $Xm \leq \{(Xa+Xb)/2\} \times 1.6$ be established. More preferably, $Xm \leq \{(Xa+Xb)/2\} \times 1.4$ is established. This equation means that there is little pitch change in the stretchable direction at the boundary of the first stretchable region E1, the intermediate region E3, and the second stretchable region.

In the case where
(4) a pitch of the bonded portions in an orthogonal direction orthogonal to a stretchable direction of the intermediate stretchable region is Ym,
(5) a pitch of the bonded portions in an orthogonal direction of the first stretchable region is Ya, and
(6) a pitch of the bonded portions in an orthogonal direction of the second stretchable region is Yb,
it is desirable that $Ym \leq \{(Ya+Yb)/2\} \times 1.6$ is established, and particularly, $Ym \leq \{(Ya+Yb)/2\} \times 1.4$ be established.

Here, the meaning of "the separation distance Px is 10 mm or less" will be described again with reference to FIG. 33. It means that when a straight line of the separation distance Px is drawn in the stretchable direction ED from the bonded portion of the first stretchable region E1, at least one center of the bonded portion of the second stretchable region E2 exists in the area of ±30° with respect to the straight line.

In the case of the intermediate region E3, it means that when a straight line of the separation distance Px is drawn in the stretchable direction ED from the bonded portion of the first stretchable region E1, at least one center of the bonded portion of the intermediate region E3 exists in the area of ±30° with respect to the straight line. In addition, it means that when a straight line of the separation distance Px is drawn in the stretchable direction ED from the bonded portion of the intermediate region E3, at least one center of the bonded portion of the second stretchable region E2 exists in the area of ±30° with respect to the straight line.

In the arrangement pattern of FIG. 29 and the arrangement pattern of FIG. 32, the separation distance Px, the separation distance Py, $Xm \leq \{(Xa+Xb)/2\}$, and $Ym \leq \{(Ya+Yb)/2\}$ were changed to examine the ratio of the occurrence of tearing of an elastic film, and the results in Tables 1 and 2 were obtained. Here, in the elastic limit length range of the stretchable region of 100 mm, the ratio of the occurrence of tearing of the elastic film represents, as a percentage, the total length of the range of the stretchable direction length (elastic limit length) in which the tearing is occurring. Note that if the tearing ratio is less than 20%, it can be determined that the external appearance is acceptable. Further, if the ratio exceeds 25%, for example, it can be determined that the appearance is partially poor at the time of wearing.

TABLE 1

FIRST STRETCHABLE REGION E1 AND SECOND STRETCHABLE REGION E2

| | Px | Py | TEARING RATIO |
|---|---|---|---|
| EXAMPLE 1 | 10 mm | 15 mm | 16% |
| EXAMPLE 2 | 7 mm | 10 mm | 1% |
| EXAMPLE 3 | 5 mm | 5 mm | 0% |
| EXAMPLE 4 | 10 mm | 10 mm | 8% |
| EXAMPLE 4 | 10 mm | 5 mm | 3% |

TABLE 2

FIRST STRETCHABLE REGION E1, INTERMEDIATE STRETCHABLE REGION E3, AND SECOND STRETCHABLE REGION E2

| | Xa | Xb | Xm | Ym | TEARING RATIO |
|---|---|---|---|---|---|
| EXAMPLE 1 | 2.5 mm | 5.0 mm | 10.0 mm | 10.0 mm | 15% |
| EXAMPLE 2 | 2.5 mm | 4.0 mm | 5.0 mm | 5.0 mm | 1% |
| EXAMPLE 3 | 2.5 mm | 2.5 mm | 2.5 mm | 4.0 mm | 0% |
| EXAMPLE 4 | 2.5 mm | 2.5 mm | 2.5 mm | 2.5 mm | 0% |

From these results, it is understood that the numerical range defined by the present invention is desirable.

INDUSTRIAL APPLICABILITY

As long as having a stretchable region which can apply the elastic sheet stretchable structure, the present invention can be applied to all disposable wearing articles such as tape-type and pad-type disposable diapers, sanitary napkins, disposable diapers for swimming and dabbling in water, etc. in addition to the above-described underpants-type disposable diaper.

10 inner member
10B inner and outer fixed region
11 top sheet
12 liquid-impervious sheet
13 absorber
13N narrowing portion
14 package sheet
17 non absorber side part
20 outer member
20A first sheet layer 20B second sheet layer
20C folded back portion
20X elastic sheet stretchable structure
21 side seal portion
23 waist end
24 waist elastic member
25F, 25f shrinkage wrinkle
29 leg around line
30 elastic film
31 bonding hole
40, 40A, 40B sheet bonded portion (first bonded portion)
41 second bonded portion
42 third bonded portion
43 fourth bonded portion
70 non-stretchable region
80 stretchable region
82 edge stretchable region
90 three-dimensional gather
93 fallen portion
94 free portion
95 gather sheet
96 gather elastic member
B back body
ED stretchable direction (width direction)
F front body
L intermediate portion
LD orthogonal direction (front-back direction)
T lower torso portion
sf small pleats
bf large pleats
Px separation distance
Py separation distance
E1 first stretchable region
E2 second stretchable region
E3 intermediate region

The invention claimed is:

1. A stretchable member, comprising:
an elastic sheet stretchable structure in which an elastic sheet is interposed between a first sheet layer having air permeability and a second sheet layer having air permeability, and the first sheet layer and the second sheet layer are bonded at a large number of fused dot-like bonded portions arranged at intervals, each of the bonded portions extending along a longitudinal axis,
wherein a stretchable region having the elastic sheet stretchable structure is capable of being expanded and contracted in a stretchable direction due to a contraction force of the elastic sheet,
the stretchable region has at least two stretchable regions including a first stretchable region and a second stretchable region,
the first stretchable region contains a plurality of rows of first bonded portions aligned in a first direction with their longitudinal axes aligned to the first direction, the rows of the first bonded portions being arranged in a second direction orthogonal to the first direction, and
the second stretchable region contains a plurality of rows of second bonded portions aligned in the second direction orthogonal to the first direction with their longitudinal axes aligned to the second direction, the rows of the second bonded portions being arranged in the first direction orthogonal to the second direction,
wherein, (1) where the first direction is inclined with respect to a direction orthogonal to the stretchable direction,
along a boundary between the first stretchable region and the second stretchable region, a separation distance in the stretchable direction and in the direction orthogonal thereto between bonded portions located on a boundary side in the stretchable direction of the first stretchable region and bonded portions located on a boundary side in the stretchable direction of the second stretchable region in an elastic limit elongation state is 10 mm or less, or (2) where the first direction is aligned to the direction orthogonal to the stretchable direction,
along a boundary between the first stretchable region and the second stretchable region, a separation distance in the stretchable direction between the bonded portions located on a boundary side in the stretchable direction of the first stretchable region and the bonded portions located on a boundary side in the stretchable direction of the second stretchable region in an elastic limit elongation state is 10 mm or less, and a separation distance in the first direction between the bonded portions in the second stretchable region is 10 mm or less.

2. The stretchable member according to claim 1, wherein the rows of the first bonded portions and the rows of the second bonded portions each intersect with the stretchable direction at an angle in a range of 30 to 150° (not including) 90°.

3. The stretchable member according to claim 1, wherein a pitch of the rows of the first bonded portions in the first direction and a pitch of the rows of the second bonded portions in the second direction are the same but shapes of the first and second bonded portions are different.

4. The stretchable member according to claim 1, wherein at least one of the rows of the first bonded portions and the rows of the second bonded portions are formed with a plurality of bonded portions having different shapes.

5. A stretchable member, comprising:
an elastic sheet stretchable structure in which an elastic sheet is interposed between a first sheet layer having air permeability and a second sheet layer having air permeability, and the first sheet layer and the second sheet layer are bonded at a large number of fused dot-like bonded portions arranged at intervals, each of the bonded portions extending along a longitudinal axis,
wherein a stretchable region having the elastic sheet stretchable structure is capable of being expanded and contracted in a stretchable direction due to a contraction force of the elastic sheet,
the stretchable region has at least two stretchable regions including a first stretchable region and a second stretchable region,
the first stretchable region contains a plurality of rows of first bonded portions aligned in a first direction with their longitudinal axes aligned to the first direction, the rows of the first bonded portions being arranged in a second direction orthogonal to the first direction, and
the second stretchable region contains a plurality of rows of second bonded portions aligned in the second direction orthogonal to the first direction with their longitudinal axes aligned to the second direction, the rows of the second bonded portions being arranged in the first direction orthogonal to the second direction,
an intermediate stretchable region is provided between the first stretchable region and the second stretchable region,
in a case where
(1) a pitch of the bonded portions in the intermediate stretchable region in a stretchable direction is Xm, (2) a pitch of the bonded portions in the first stretchable region in a stretchable direction is Xa, and
(3) a pitch of the bonded portions in the second stretchable region in a stretchable direction is Xb,
$Xm \leq \{(Xa+Xb)/2\} \times 1.6$ is established,
wherein, (1) where the first direction is inclined with respect to a direction orthogonal to the stretchable direction,
a separation distance in the stretchable direction and in the direction orthogonal thereto between bonded portions located on a first-stretchable-region side in the stretchable direction of the intermediate stretchable region and bonded portions located on an intermediate-stretchable-region side in the stretchable direction of the first stretchable region in an elastic limit elongation state is 10 mm or less,
a separation distance in the first direction between bonded portions in the intermediate stretchable region is 10 mm or less,
a separation distance in the stretchable direction and in the direction orthogonal thereto between bonded portions located on the second-stretchable-region side in the stretchable direction of the intermediate stretchable region and bonded portions located on the intermediate-stretchable-region side in the stretchable direction of the second stretchable region in an elastic limit elongation state is 10 mm or less, or
(2) where the first direction is aligned to the direction orthogonal to the stretchable direction,
a separation distance in the stretchable direction between bonded portions located on a first-stretchable-region side in the stretchable direction of the intermediate stretchable region and bonded portions located on an intermediate-stretchable-region side in the stretchable direction of the first stretchable region in an elastic limit elongation state is 10 mm or less,
a separation distance in the stretchable direction between bonded portions located on second-stretchable-region side in the stretchable direction of the intermediate stretchable region and bonded portions located on the intermediate-stretchable-region side in the stretchable direction of the second stretchable region in an elastic limit elongation state is 10 mm or less, and a separation distance in the first direction between the bonded portions in the intermediate-stretchable region and the bonded portions in the second stretchable region is 10 mm or less.

6. The stretchable member according to claim 5, wherein, in a case where,
(4) a pitch of the bonded portions in the orthogonal direction in the intermediate stretchable region is Ym,
(5) a pitch of the bonded portions in the orthogonal direction orthogonal to the stretchable direction in the rows of the first bonded portions is Ya, and
(6) a pitch of the bonded portions in the orthogonal direction orthogonal to the stretchable direction in the rows of the second bonded portions is Yb,
$Ym \leq \{(Ya+Yb)/2\} \times 1.6$ is established.

7. The stretchable member according to claim 5, wherein and the rows of the first bonded portions and the rows of the second bonded portions each intersect with the stretchable direction at an angle in a range of 30 to 150° (not including) 90°.

8. An underpants type disposable wearing article comprising:
an outer body integrally provided from a front body to a back body or an outer body separately provided on the front body and the back body;
an inner body attached to an intermediate portion in a width direction of the outer body and provided over both front and back sides of a crotch portion;
side seal portions in which both side portions of the outer body in the front body and both side portions of the outer body in the back body are bonded respectively;
a waist opening; and
a pair of right and left leg openings,
wherein the outer body includes a stretchable member, comprising:
an elastic sheet stretchable structure in which an elastic sheet is interposed between a first sheet layer having air permeability and a second sheet layer having air permeability, and the first sheet layer and the second sheet layer are bonded at a large number of fused dot-like bonded portions arranged at intervals, each of the bonded portions extending along a longitudinal axis,
wherein a stretchable region having the elastic sheet stretchable structure is capable of being expanded and contracted in a stretchable direction due to a contraction force of the elastic sheet,
the stretchable region has at least two stretchable regions including a first stretchable region and a second stretchable region,
the first stretchable region contains a plurality of rows of first bonded portions aligned in a first direction with their longitudinal axes aligned to the first direction, the rows of the first bonded portions being arranged in a second direction orthogonal to the first direction, and
the second stretchable region contains a plurality of rows of second bonded portions aligned in the second direction orthogonal to the first direction with their longitudinal axes aligned to the second direction, the rows of the second bonded portions being arranged in the first direction orthogonal to the second direction,
wherein, (1) where the first direction is inclined with respect to a direction orthogonal to the stretchable direction,
along a boundary between the first stretchable region and the second stretchable region, a separation distance in the stretchable direction and the direction orthogonal thereto between bonded portions located on a boundary side in the stretchable direction of the first stretchable region and bonded portions located on a boundary side in the stretchable direction of the second stretchable region in an elastic limit elongation state is 10 mm or less, or
(2) where the first direction is aligned to the direction orthogonal to the stretchable direction,
along a boundary between the first stretchable region and the second stretchable region, a separation distance in the stretchable direction between the bonded portions located on a boundary side in the stretchable direction of the first stretchable region and the bonded portions located on a boundary side in the stretchable direction of the second stretchable region in an elastic limit elongation state is 10 mm or less, and a separation distance in the first direction between the bonded portions in the second stretchable region is 10 mm or less, and
wherein the outer body in at least one of the front body and the back body has the elastic sheet stretchable structure extending over an extension in its width direction corresponding to an extension between the side seal portions at least partly in its front-back direction, with the stretchable direction of the stretchable region arranged in the width direction of the outer body.

* * * * *